United States Patent
Bolsöy

(10) Patent No.: US 11,413,262 B2
(45) Date of Patent: *Aug. 16, 2022

(54) PHARMACEUTICAL COMPOSITIONS COMPRISING LEVODOPA, A DOPAMINE DECARBOXYLASE INHIBITOR AND A COMT INHIBITOR AND METHOD OF ADMINISTRATION THEREOF

(71) Applicant: Intrance International AB, Uppsala (SE)

(72) Inventor: Roger Bolsöy, Uppsala (SE)

(73) Assignee: Intrance International AB, Uppsala (SE)

(*) Notice: Subject to any disclaimer, the term of this patent is extended or adjusted under 35 U.S.C. 154(b) by 0 days.

This patent is subject to a terminal disclaimer.

(21) Appl. No.: 16/992,824

(22) Filed: Aug. 13, 2020

(65) Prior Publication Data
US 2021/0023033 A1     Jan. 28, 2021

Related U.S. Application Data

(62) Division of application No. 16/054,392, filed on Aug. 3, 2018, now Pat. No. 10,786,472, which is a division
(Continued)

(30) Foreign Application Priority Data

Sep. 4, 2014 (SE) .................................. 1451034-1
Mar. 24, 2015 (SE) .................................. 1550344-4

(51) Int. Cl.
*A61K 31/198*     (2006.01)
*A61K 9/00*       (2006.01)
(Continued)

(52) U.S. Cl.
CPC .......... *A61K 31/198* (2013.01); *A61K 9/0019* (2013.01); *A61K 9/0024* (2013.01); *A61K 9/06* (2013.01); *A61K 9/1652* (2013.01); *A61K 31/165* (2013.01); *A61K 31/277* (2013.01); *A61K 45/06* (2013.01); *A61K 47/38* (2013.01)

(58) Field of Classification Search
None
See application file for complete search history.

(56) References Cited

U.S. PATENT DOCUMENTS

| 5,635,213 A | 6/1997 | Nystrom et al. |
| 6,500,867 B1 | 12/2002 | Virkki et al. |

(Continued)

FOREIGN PATENT DOCUMENTS

| CN | 1845728 A | 10/2006 |
| CN | 101636145 A | 1/2010 |

(Continued)

OTHER PUBLICATIONS

AbbVie Limited, Duodopa intestinal gel, Medicines.org, 7 pages (2014).

(Continued)

*Primary Examiner* — Aradhana Sasan
(74) *Attorney, Agent, or Firm* — Choate, Hall & Stewart LLP; Brenda Herschbach Jarrell; Rebekah Z. Kitto

(57) ABSTRACT

A pharmaceutical gel composition for intra-intestinal administration comprises (i) a dopamine replacement agent, (ii) a dopamine decarboxylase inhibitor (DDI), and (iii) a COMT inhibitor.

22 Claims, 4 Drawing Sheets

Related U.S. Application Data of application No. 15/507,959, filed as application No. PCT/SE2015/050939 on Sep. 4, 2015, now Pat. No. 10,071,069.

(51) Int. Cl.

| | | |
|---|---|---|
| A61K 47/38 | (2006.01) | |
| A61K 9/06 | (2006.01) | |
| A61K 31/277 | (2006.01) | |
| A61K 45/06 | (2006.01) | |
| A61K 31/165 | (2006.01) | |
| A61K 9/16 | (2006.01) | |

(56) References Cited

U.S. PATENT DOCUMENTS

| | | |
|---|---|---|
| 6,797,732 B2 | 9/2004 | Virkki et al. |
| 10,071,069 B2 | 9/2018 | Bolsoy |
| 10,555,922 B2 | 2/2020 | Bolsoy |
| 10,786,472 B2 | 9/2020 | Bolsoy |
| 2006/0222703 A1 | 10/2006 | Politi |
| 2010/0221321 A1 | 9/2010 | Miller et al. |
| 2013/0253056 A1 | 9/2013 | Nemas et al. |
| 2016/0151317 A1 | 6/2016 | Yacoby-Zeevi et al. |
| 2017/0231937 A1 | 8/2017 | Bolsoy |
| 2018/0243250 A1 | 8/2018 | Bolsoy |
| 2018/0338944 A1 | 11/2018 | Bolsoy |

FOREIGN PATENT DOCUMENTS

| | | |
|---|---|---|
| CN | 102438587 A | 5/2012 |
| EP | 0670713 B1 | 9/1999 |
| EP | 1670450 A2 | 6/2006 |
| SE | 1451034 A1 | 3/2016 |
| WO | WO-2005/099678 A1 | 10/2005 |
| WO | WO-2007/138086 A1 | 12/2007 |
| WO | WO-2008/053297 A2 | 5/2008 |
| WO | WO-2009/098661 A1 | 8/2009 |
| WO | WO-2010/134074 A1 | 11/2010 |
| WO | WO-2012/066538 A1 | 5/2012 |
| WO | WO-2012/147099 A1 | 11/2012 |
| WO | WO-2014/141261 A1 | 9/2014 |
| WO | WO-2017/039525 A1 | 3/2017 |

OTHER PUBLICATIONS

Ahtila, S. et al., Effect of Entacapone, a COMP inhibitor, on the Pharmacokinetics and Metabolism of Levodopa After Administration of Controlled-Release Levodopa-Cardibopa in Volunteers, Clinical Neuropharmacology, 18(1):46-57 (1995).

Brodsky, M.A. et al., Sleepiness in Parkinson's disease: a controlled study, Movement Disorders, 18:667-672 (2003).

Brooks, D.J. et al., Entacapone is beneficial in both fluctuating and non-fluctuating patients with Parkinson's disease: a randomised, placebo controlled, double blind, six month study, J Neurol Neurosurg Psychiatry, 74:1071-1079 (2003).

Cabrini, S. et al., Preliminary evaluation of the DDS-PC inventory a new tool to assess impulsive-compulsive behaviors associated to dopamine replacement therapy in Parkinson's disease, Neurol Sci, 30:307-313 (2009).

Deuschl, G. et al., A randomized trial of deep-brain stimulation for Parkinson's disease, N Engl J Med, 355:896-908 (2006).

Esselink, R.A.J. et al., Unilateral pallidotomy versus bilateral subthalamic nucleus stimulation in PD—a randomized trial, Neurology, 62:201-207 (2004).

European Medicines Agency, EMA—Stalevo: EPAR-Product Information, Annex 1, pp. 2-13, retrieved from the internet: http://www.ema.europa.eu/docs/en_GB/document_library/EPAR_Product_Information/human/000511/WC500057485.pdf, p. 3, paragraph [0005]; in particular, section 2, section 4.1 and section 4.2 (2016).

Evans, A.H. et al., Funding in Parkinson's disease: its relation to the dopamine dysregulation syndrome, Mov Disord, 19:397-405 (2004).

Fan, W.H. et al., Impulse control disorders in Parkinson's disease in a Chinese population, Neurosci Lett, 465:6-9 (2009).

Fine, J. et al., Long-term follow-up of unilateral pallidotomy in advanced Parkinson's disease, N Engl J Med, 342:1708-1714 (2000).

Forsberg, M. et al., Pharmacokinetics and Pharmacodynamics of Entacapone and Tolcapone after Acut eand Repeated Administration: A Comparative Study in the Rat, The Journal of Pharmacology and Experimental Therapeutics, 304(2):498-506 (2003).

Gao, B-W. et al., Current Clinical Progress of COMT Inhibitor, Progress in Modern Biomedicine, 14(5):982-985 (2014) English Abstract.

Hauser, R.A. et al., Double-blind trial of levodopa/carbidopa/entacapone versus levodopa/carbidopa in early Parkinson's disease, Movement Disorders, 24(4):541-550 (2009).

Hauser, R.A et al., Levodopa/carbidopa/entacapone (Stalevo), Neurology, 62(1):suppl 1 (2004).

Hobson, D.E. et al., Excessive daytime sleepiness and sudden-onset sleep in Parkinson disease—a survey by the Canadian Movement Disorders Group, JAMA, 287:455-463 (2002).

International Search Report for PCT/SE2015/050939, 9 pages (dated Jan. 26, 2016).

International Search Report for PCT/SE2016/050828, 9 pages (dated Dec. 9, 2016).

Kaakkola, S. et al., Entacapone in combination with standard or controlled-release levodopa/carbidopa: a clinical and pharmacokinetic study in patients with Parkinson's disease, European Journal of Neurology, 2(4):341-347 (1995).

Katzenschlager, R. et al., Fourteen-year final report of the randomized PDRG-UK trial comparing three initial treatments in PD, Neurology, 71:474-480 (2008).

Koller, W. et al., An open-label evaluation of the tolerability and safety of Stalevo® (carbidopa, levodopa and entacapone) in Parkinson's disease patients experiencing wearing-off, Journal of Neural Transmission, 112(2):221-230 (2005).

Kuoppamaki, M. et al., Comparison of pharmacokinetic profile of levodopa throughout the day between levodopa/carbidopa/entacapone and levodopa/carbidopa when administered four or five times daily, Eur J Clin Pharmacol, 65:443-455 (2009).

Moller, J.C. et al., Pharmacotherapy of Parkinson's disease in Germany, J Neurol, 252:926-935 (2005).

Nyholm, D. et al., Levodopa infusion combined with entacapone ortolcapone in Parkinson disease: a pilot trial, European Journal of Neurology, 19:820-826 (2012).

Olanow, C.W. et al., Continuous intrajejunal fusion of levodoopa-carbidopa intestinal gel for patients with advanced Parkinson's disease: a randomised, controlled, double-blind, double-dummy study, Lancet Neurology, 13:141-149 (2014).

Olanow, C.W. et al., Double-Blind, Double-Dummy, Randomized Study of Continuous Intrajejunal Infusion of Levodopa-Carbidopa Intestinal Gel in Advanced Parkinson's Disease, Lancet Neurol, 13(2):141-149 (2014).

Ondo, W.G. et al., Subthalamic deep brain stimulation in patients with a previous pallidotomy, Mov Disord, 21:1252-1254 (2006).

Peralta, C.M. et al., Restless legs syndrome in Parkinson's disease, Mov Disord, 24:2076-2080 (2009).

Reimer, J. et al., Use and interpretation of on/off diaries in Parkinson's disease, J Neurol Neurosurg Psychiatry, 75:396-400 (2004).

Sethi, K.D. et al., Levodopa/carbidopa/entacapone 200/50/200 mg (Stalevo 200) in the treatment of Parkinson's disease: a case series, Cases Journal, 2:7134, 5 pages (2009).

Shihong, W. et al., Experimental Study on Forced Degradation of Levodopa, China Pharmaceuticals, pp. 20-21 (2008) English Abstract.

Solla, P. et al., Therapeutic interventions and adjustments in the management of Parkinson disease: role of combined carbidopa/levodopa/entacapone (Stalevo), Neuropsychiatric disease and treatment, 6:483-490 (2010).

Tomlinson, C.L. et al., Systematic Review of Levodopa Dose Equivalency Reporting in Parkinson's Disease, Movement Disorders, 25(15):2649-2685 (2010).

(56) References Cited

OTHER PUBLICATIONS

Vingerhoets, F.J.G. et al., Subthalamic DBS replaces levodopa in Parkinson's disease—two-year follow-up, Neurology, 58:396-401 (2002).
Wenzelburger, R. et al., Force overflow and levodopa-induced dyskinesias in Parkinson's disease, Brain, 125:871-879 (2002).
Written Opinion for PCT/SE2015/050939, 7 pages (dated Jan. 26, 2016).
Written Opinion for PCT/SE2016/050828, 15 pages (dated Dec. 9, 2016).
Yuan, L. J. and Ji, L., Pharmacology and clinical evaluation of a new antiparkinsonian agent entacapone, Chinese Journal of Neww Drugs, 16(2):171-174 (2007) English Abstract.

PHARMACEUTICAL COMPOSITIONS COMPRISING LEVODOPA, A DOPAMINE DECARBOXYLASE INHIBITOR AND A COMT INHIBITOR AND METHOD OF ADMINISTRATION THEREOF

CROSS REFERENCE TO RELATED APPLICATIONS

This application is a divisional of U.S. patent application Ser. No. 16/054,392, filed Aug. 3, 2018, which issued as U.S. Pat. No. 10,786,472 on Sep. 29, 2020, which is a divisional of U.S. patent application Ser. No. 15/507,959, filed Mar. 1, 2017, which issued as U.S. Pat. No. 10,071,069 on Sep. 11, 2018, which is a national stage entry of PCT/SE2015/050939, filed Sep. 4, 2015, which claims priority to and the benefit of each of Sweden Patent Application No. 1451034-1, filed Sep. 4, 2014 and Sweden Patent Application No. 1550344-4, filed Mar. 24, 2015, the contents of all of which are herein incorporated by reference in their entireties.

BACKGROUND

Neurodegenerative disorders result when neurons normally do not reproduce or replace themselves, thus damaged neurons cannot be replaced. Progressive degeneration and/or death of neuronal cells often results in problems with movement (e.g., ataxias), or mental functioning (e.g., dementias). Many neurodegenerative disorders are currently considered to be incurable. Examples of neurodegenerative disorders include Parkinson's disease ("PD"), Alzheimer's disease ("AD"), and Huntington's disease ("HD").

Parkinson's disease is characterized by a progressive degeneration of the dopaminergic pathway resulting in reduced concentration of the neurotransmitter dopamine in the brain which manifests itself as symptoms of slowness of movement (e.g., bradykinesia), rigidity, tremor and poor balance in the patient.

Biochemically, dopamine (3,4-dihydroxyphenethylamine) is formed by metabolism of dopamine precursors. For example, dopamine is formed by decarboxylation of the precursor levodopa (L-dopa; L-3,4-dihydroxyphenylalanine) through the enzyme aromatic L-amino acid decarboxylase (also known as DOPA decarboxylase (DDC)), both in the brain and in the peripheral circulation. Levodopa is in turn produced from the amino acid L-tyrosine by the enzyme tyrosine hydroxylase (TH).

Dopamine is metabolized to homovanillic acid (HVA) mainly through two metabolic pathways, namely (i) via 3,4-dihydroxyphenylacetic acid (DOPAC) by the enzymes monoamine oxidase (MAO) and catechol-O-methyltransferase (COMT), and (ii) via 3-methoxytyramine by the enzymes catechol-O-methyltransferase (COMT) and monoamine oxidase (MAO).

The most common treatment of PD aims at restoring the dopamine concentration in the brain. Administration of dopamine is ineffective because it does not cross the blood-brain barrier. However, since the precursor levodopa does cross the blood-brain barrier, and is converted to dopamine in the brain, administration of levodopa has for a long time been, and still is, the drug of first choice for PD treatment.

SUMMARY

The present invention provides particular compositions and strategies for treating certain dopamine-related diseases, disorders and conditions, including certain neurodegenerative disorders (e.g., Parkinson's Disease (PD)) and/or for administering agents useful in such treatment. Among other things, the present invention encompasses identification of the source of a problem with certain known compositions and/or strategies for treating such diseases, disorders or conditions and/or for administering relevant agents.

In some embodiments, the present disclosure encompasses the insight that administering a combination of agents that includes each of (i) a dopamine replacement agent, (ii) a dopamine decarboxylase inhibitor (DDI), and (iii) a COMT inhibitor to a subject, particularly when one or more of the agents is delivered by intra-intestinal administration of a pharmaceutical gel, provides certain unexpected advantages and/or solves one or more problems associated with prior strategies for treating neurodegenerative disorders (e.g., PD).

In some embodiments, the present disclosure provides methods in which a COMT inhibitor is administered in combination with therapy that involves administering a dopamine replacement agent and/or a DDI by intra-intestinal administration of a pharmaceutical gel.

In some embodiments, the present invention encompasses the insight that in various contexts may be useful to deliver a COMT inhibitor by intra-intestinal administration of a pharmaceutical gel, and provides particular methods and reagents relating thereto.

Among other things, the present invention encompasses identification of the source of a problem with certain known compositions and/or strategies for administering a dopamine replacement agent (e.g., levodopa). For example, the present disclosure encompasses the recognition of a need for treatment strategies that minimize a subject's intake of and/or exposure to the metabolic precursor, while maintaining therapeutic benefit of such intake or exposure. The present disclosure provides such treatment strategies (e.g., compositions and/or methods that achieve reduced patient exposure, while maintaining therapeutic benefit, as compared with a relevant reference strategy (e.g., a currently accepted standard therapy).

In some embodiments, the present disclosure encompasses the recognition of a need for improved pharmaceutical compositions for intra-intestinal administration of a dopamine replacement agent, and particularly of levodopa. The present disclosure provides such compositions.

In some embodiments, the present disclosure identifies the source of a problem with storage characteristics (e.g., stability to long term storage and/or storage under particular conditions) of certain compositions comprising a dopamine replacement agent, and particularly of compositions comprising levodopa. Among other things, the present disclosure encompasses the recognition of a need for pharmaceutical compositions comprising dopamine replacement agents, and particularly of compositions comprising levodopa, which have particular storage stability characteristics. The present disclosure provides such compositions.

In many embodiments, intra-intestinal administration typically is duodenal and/or jejunal administration via an external access point.

In some embodiments, a pharmaceutical gel composition for intra-intestinal administration comprises a dopamine replacement agent, a dopamine decarboxylase inhibitor (DDI), and a catechol-O-methyltransferase (COMT) inhibitor.

In some particular embodiments, the present invention provides a pharmaceutical gel composition for intra-intestinal administration, comprising at least about 10 mg/ml of levodopa and at least about 2.5 mg/ml of a dopamine decarboxylase inhibitor, wherein the gel composition further comprises at least about 10 mg/ml of a COMT inhibitor.

In certain provided gel compositions and/or methods, one or more active compounds (e.g., levodopa and/or one or more DDIs [e.g., carbidopa] and/or one or more COMT inhibitors [e.g., entacapone]) may be provided and/or utilized in the form of a pharmaceutically acceptable salt thereof, and/or in a hydrate or solvate form thereof. In some particular embodiments, certain compositions and/or methods may utilize one or more active compounds may be provided and/or utilized in a solid form; in some such embodiments, the solid form may be or comprise a crystalline form; in some such embodiments, the solid form may be or comprise an amorphous form. In some embodiments, a solid form comprises or consists of an amorphous form, or a single particular crystalline form.

In some embodiments, a pharmaceutical gel composition comprises at most 200 mg/ml of levodopa, at most 50 mg/ml of a dopamine decarboxylase inhibitor, and at most 200 mg/ml of a COMT inhibitor.

Exemplary dopamine decarboxylase inhibitors include carbidopa, benzerazide, α-difluoromethyldopa [(2S)-2-amino-2-[3,4-dihydroxyphenyl)-methyl]-3,3-difluoropropanoic acid] and α-methyldopa [(S)-2-amino-3-[3,4-dihydroxyphenyl)-2-methyl-propanoic acid].

In some embodiments, a dopamine decarboxylase inhibitor is carbidopa, benserazide, or any combination thereof.

In some embodiments, a dopamine decarboxylase inhibitor is carbidopa.

In some embodiments, a COMT inhibitor is selected from the group consisting of entacapone, tolcapone, opicapone and any combination thereof.

In some embodiments, a COMT inhibitor is entacapone.

In some embodiments, a pharmaceutical gel composition comprises a DDI such as carbidopa, and further comprises a substance capable of inhibiting degradation of carbidopa to hydrazine.

In some embodiments, a substance capable of inhibiting degradation of carbidopa to hydrazine comprises entacapone.

In some embodiments, a pharmaceutical gel composition comprises about 20 mg/ml of levodopa, 5 mg/ml of carbidopa, and 20 mg/ml of entacapone.

In some embodiments, a pharmaceutical gel composition as described herein that comprises one or more COMT inhibitors and at least one additional active compound is characterized by increased stability (e.g., reduced degradation) of the at least one additional active compound, for example relative to that observed for an otherwise comparable composition lacking (or, in some embodiments, containing a different absolute or relative amount of) the COMT inhibitor. In some such embodiments, stability is assessed over time (e.g., after a particular period of time has elapsed) and/or under particular storage conditions. For example, in some embodiments, such increased stability is observed over a period of time that extends for at least 1 week, 2 weeks, 5 weeks, 7 weeks, 10 weeks, 15 weeks, 20 weeks or more, for example under refrigerated conditions (e.g., conditions under which the composition(s) is/are maintained at a temperature below about 15° C. and, preferably, within a range of about 0° C. to about 15° C., about 0° C. to about 12° C., about 0° C. to about 10° C., about 0° C. to about 8° C., or about 2° C. to about 8° C.).

In some embodiments, a provided intra-intestinal gel composition comprises and/or is prepared from a gel characterized by a pH not higher than about 5.7 and/or is maintained at a pH not higher than about 5.7. In some embodiments, such provided compositions that include one or more active agents (e.g., levodopa, a DDI, a COMT inhibitor, etc.) are characterized by improved stability of one or more such active agents as compared with a relevant reference composition that differs, for example, in value of pH.

In some embodiments, an intra-intestinal gel composition is deoxygenized (e.g., via nitrogen purging). In some embodiments, such provided compositions that include one or more active agents are characterized by improved stability of one or more such active agents as compared with a relevant reference composition that differs, for example, in presence and/or duration of such deoxygenization.

In some embodiments, a pharmaceutical gel composition includes antioxidants (e.g., ascorbic acid or citric acid). In some embodiments, such provided compositions that include one or more active agents are characterized by improved stability of one or more such active agents as compared with a relevant reference composition that differs, for example, in presence and/or amount (e.g., absolute or relative values) of such antioxidants.

In some embodiments, deoxygenation is combined with lowered pH or antioxidant.

In some embodiments, a provided gel composition is substantially free of (e.g., lacks detectable and/or material levels of) a metal chelating agent, such as EDTA; in some embodiments, a provided gel composition is substantially free of any metal chelating agent.

In some embodiments, a pharmaceutical gel composition is provided in a light-protected container.

In some embodiments, one or more active substances, (e.g., levodopa, dopamine carboxylase inhibitor (e.g., carbidopa) and COMT inhibitor (e.g., entacapone) are in the form of particles, for example having a maximum particle size not exceeding about 80 μm, which particles may, in some embodiments, be suspended in a carrier (e.g., in an aqueous carrier); in some such embodiments, the carrier has a viscosity of at least 300 mPas, measured at a moderate shear rate.

In some embodiments, viscosity of an intra-intestinal gel composition is at least 1800 mPas. In another embodiment, the viscosity is in the range of 2200 to 4500 mPas.

While a carrier typically may be of polysaccharide type, and, for example, be selected from cellulose, methyl cellulose (MC), ethyl cellulose, carboxymethyl cellulose (CMC) and salts thereof, xanthan gum, carrageenan, and combinations thereof the carrier may also be a synthetic polymer, such as polyvinylpyrrolidone (PVP; Povidon) or polyacrylic acid (PAA; Carbomer). An exemplary carrier is the sodium salt of carboxymethyl cellulose (NaCMC).

In some embodiments, a pharmaceutical gel composition comprises about 2% (w/w) micronized levodopa, about 0.5% (w/w) micronized carbidopa, 2 about % (w/w) micronized entacapone, and 2.92 about % (w/w) sodium carboxymethyl cellulose.

In some embodiments, a pH value of a pharmaceutical gel composition is selected to be the lowest pH value equal to or greater than about 5.0 to about 5.5 where viscosity of an aqueous carrier after 12 days at 25° C. is at least 300 mPas at a moderate shear rate.

In some embodiments, a carrier of a pharmaceutical gel composition is NaCMC, and the pH value is 5.5±0.2.

In some aspects of the present invention provides a pharmaceutical gel composition for a treatment of neurodegenerative disorders (e.g., Parkinson's Disease).

In some aspects of the present invention, there is provided a method of treating Parkinson's Disease, which comprises intra-intestinally administering a pharmaceutical gel composition according to certain aspects of the present invention as described above.

In some embodiments, a pharmaceutical gel composition is administered continuously over a period less than about 16 hours per day.

In some embodiments, a pharmaceutical gel composition is administered continuously over a period greater than about 16 hours per day.

In some embodiments, a pharmaceutical gel composition is administered continuously as a long-term treatment for more than 1 day.

In some aspects, the present invention provides use of entacapone in a pharmaceutical gel composition comprising levodopa and carbidopa for inhibiting degradation of carbidopa to hydrazine.

In some embodiments, a pharmaceutical gel composition comprises a pharmaceutically active agent and formulated for intra-intestinal delivery, wherein the pharmaceutically active agent is or comprises entacapone.

In some embodiments, a pharmaceutical gel composition for intra-intestinal administration comprises levodopa, a dopamine decarboxylase inhibitor and a COMT inhibitor, wherein the weight ratio of the COMT inhibitor to the dopamine decarboxylase inhibitor is about 10:1 to about 2:1, or about 5:1 to about 3:1.

In some embodiments, a pharmaceutical gel composition for intra-intestinal administration comprises levodopa, a dopamine decarboxylase inhibitor, and a COMT inhibitor, wherein the weight ratio of the dopamine decarboxylase inhibitor to levodopa is at least about 1:10.

In some embodiments, a pharmaceutical gel composition for intra-intestinal administration comprises levodopa, a dopamine decarboxylase inhibitor, and a COMT inhibitor, wherein the levodopa, the dopamine decarboxylase inhibitor and the COMT inhibitor are in the form of particles, and the particles are suspended in an aqueous carrier, and have the particle size of no greater than about 80 μm.

In some embodiments, a method of prolonging shelf life of a pharmaceutical gel comprises providing a first gel comprising levodopa and a dopamine decarboxylase inhibitor and including a COMT inhibitor in the first gel.

In some embodiments, a method for reducing hydrazine production and/or accumulation in a pharmaceutical composition comprise levodopa and carbidopa and/or upon its administration comprises a step of including a COMT inhibitor in the pharmaceutical compositions.

Some embodiments are set forth in the dependent claims.

A more complete understanding of the invention, as well as further features and advantages thereof, will be obtained by reference to the following detailed description read in conjunction with the accompanying drawings.

DEFINITIONS

Figure 1:
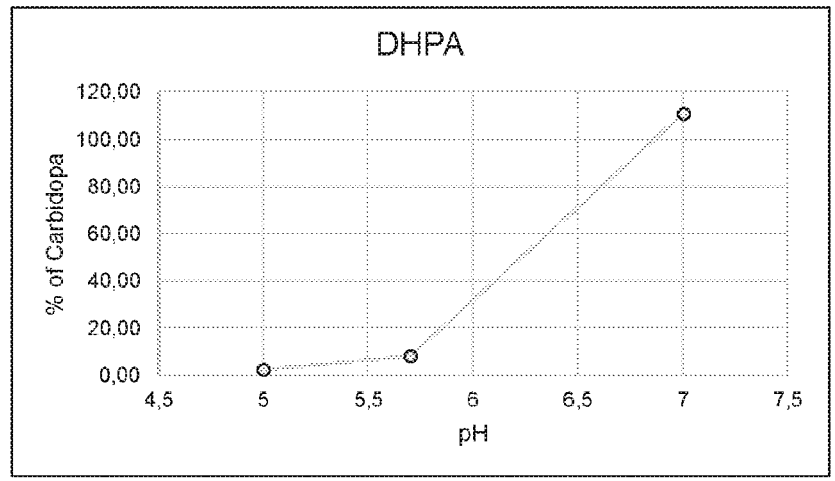
FIG. 1 is a graph showing an exemplary level of carbidopa degradation product DHPA versus pH at the end of a 10 days stability test at 25° C. on a levodopa/carbidopa/entacapone gel formulation.

As used herein, the term "activating agent" refers to an agent whose presence or level correlates with elevated level or activity of a target, as compared with that observed absent the agent (or with the agent at a different level). In some embodiments, an activating agent is one whose presence or level correlates with a target level or activity that is comparable to or greater than a particular reference level or activity (e.g., that observed under appropriate reference conditions, such as presence of a known activating agent, e.g., a positive control).

As used herein, the term "administration" refers to the administration of a composition to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, within a specific organ (e.g. intrahepatic), mucosal, nasal, oral, rectal, subcutaneous, sublingual, topical, tracheal (including by intratracheal instillation), transdermal, vaginal and vitreal. In some embodiments, administration may involve intermittent dosing. In some embodiments, administration may involve continuous dosing (e.g., perfusion) for at least a selected period of time. As is known in the art, antibody therapy is commonly administered parenterally (e.g., by intravenous or subcutaneous injection).

As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Two events or entities are "associated" with one another, as that term is used herein, if the presence, level and/or form of one is correlated with that of the other. For example, a particular entity (e.g., polypeptide, genetic signature, metabolite, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

As used herein, the term "carrier" refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

As used herein, the term "combination therapy" refers to those situations in which a subject is simultaneously exposed to two or more therapeutic regimens (e.g., two or more therapeutic agents). In some embodiments, two or more agents or may be administered simultaneously; in some embodiments, such agents may be administered sequentially; in some embodiments, such agents are administered in overlapping dosing regimens.

A "composition" or a "pharmaceutical composition" according to this invention refers to the combination of two or more agents as described herein for co-administration or administration as part of the same regimen. It is not required in all embodiments that the combination of agents result in physical admixture, that is, administration as separate co-agents each of the components of the composition is possible; however many patients or practitioners in the field may find it advantageous to prepare a composition that is an admixture of two or more of the ingredients in a pharmaceutically acceptable carrier, diluent, or excipient, making it possible to administer the component ingredients of the combination at the same time.

As used herein, the term "comparable" refers to two or more agents, entities, situations, sets of conditions, etc., that may not be identical to one another but that are sufficiently similar to permit comparison there between so that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

The term "dopamine replacement agent", as used herein, refers to an agent whose administration to a human, correlates with increased dopamine levels in the brain as compared with those observed absent such administration. In some embodiments, a dopamine replacement agent is characterized by an ability to cross the blood-brain barrier. In some embodiments, a dopamine replacement agent is selected from the group consisting of metabolic precursors of dopamine (e.g., levodopa, melevodopa, etilevodopa etc and combinations thereof), dopamine agonists (e.g., apomorphine, bromocriptine, cabergoline, dihydroergocristine mesylate, pergolide, piribedil pramipexole, ropinirole, rotigotine, etc and combinations thereof), agents that block dopamine degradation (e.g., MAO-B inhibitors such as selegiline, rasagiline, etc. and combinations thereof) and/or agents (e.g., budipine) that otherwise stimulate dopamine production. Various commercial formulations and preparations of such agents are known in the art, including certain oral (e.g., capsule or tablet), transdermal (e.g., patch), parenteral (e.g., subcutaneous, intravenous, intrathecal, etc., particularly for infusion), and/or other (e.g., gel, and particularly intra-intestinal gel) formulations.

As used herein, the term "dosage form" refers to a physically discrete unit of an active agent (e.g., a therapeutic or diagnostic agent) for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount In some embodiments, a dosing regimen is correlated with a desired or beneficial outcome when administered across a relevant population (i.e., is a therapeutic dosing regimen).

As used herein, the term "excipient" refers to a non-therapeutic agent that may be included in a pharmaceutical composition, for example to provide or contribute to a desired consistency or stabilizing effect. Suitable pharmaceutical excipients include, for example, starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like.

As used herein, the term "gel" refers to a viscoelastic material whose rheological properties distinguish it from, for example, a solution, a solid, etc. In some embodiments, a material or composition is considered to be a gel if its storage modulus (G') is larger than its modulus (G"). In some embodiments, a composition is considered to be a gel if there are chemical or physical cross-linked networks in solution, for example as distinguished from entangled molecules in viscous solution. In some embodiments, a gel composition may be or comprise particles of a first material suspended or otherwise distributed within a matrix. In some embodiments, a matrix is or comprises polysaccharide type, and, for example, be selected from cellulose, methyl cellulose (MC), ethyl cellulose, carboxymethyl cellulose (CMC) and salts thereof, xanthan gum, carrageenan, and combinations thereof the carrier may also be a synthetic polymer, such as polyvinylpyrrolidone (PVP; Povidon) or polyacrylic acid (PAA; Carbomer). An exemplary carrier is the sodium salt of carboxymethyl cellulose (NaCMC).

As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions (e.g., a dopamine-related disease, disorder or condition, for example a neurodegenerative disorder such as PD). In some embodiments, a patient displays one or more symptoms of a disease, disorder or condition. In some embodiments, a patient has been diagnosed with one or more diseases, disorders or conditions. In some embodiments, the patient is receiving or has received certain therapy to diagnose and/or to treat a disease, disorder, or condition.

As used herein, the term "pharmaceutical composition" refers to a composition in which an active agent is formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

The term "shear rate" as used herein refers to a rate at which a progressive deformation of a material substance in which parallel internal surfaces slide past one another is applied to some material. A "moderate shear rate" as used herein refers to the shear rate when the aqueous carrier is moderately agitated, typically corresponding to a shear rate of less than approximately 500 $s^{-1}$ but higher than approximately 20 $s^{-1}$ where the carrier is almost at rest.

The term "stable," when applied to compositions herein, means that the compositions maintain one or more aspects of their physical structure and/or activity over a period of time under a designated set of conditions. In some embodiments, the period of time is at least about one hour; in some embodiments the period of time is about 5 hours, about 10 hours, about one (1) day, about one (1) week, about two (2) weeks, about one (1) month, about two (2) months, about three (3) months, about four (4) months, about five (5) months, about six (6) months, about eight (8) months, about ten (10) months, about twelve (12) months, about twenty-four (24) months, about thirty-six (36) months, or longer. In some embodiments, the period of time is within the range of about one (1) day to about twenty-four (24) months, about two (2) weeks to about twelve (12) months, about two (2) months to about five (5) months, etc. In some embodiments, the designated conditions are ambient conditions (e.g., at room temperature and ambient pressure). In some embodiments, the designated conditions are physiologic conditions (e.g., in vivo or at about 37° C. for example in serum or in phosphate buffered saline). In some embodiments, the designated conditions are under cold storage (e.g., at or below about 4° C., −20° C., or −70° C.). In some embodiments, the designated conditions are in the dark.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

As used herein, the phrase "therapeutic agent" or "active agent" (e.g., "active compound") in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

As used herein, the term "therapeutically effective amount" is meant an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

As used herein, the term "treatment" (also "treat" or "treating") refers to any administration of a substance (e.g., anti-receptor tyrosine kinases antibodies or receptor tyrosine kinase antagonists) that partially or completely alleviates, ameliorates, relives, inhibits, delays onset of, reduces severity of, and/or reduces incidence of one or more symptoms, features, and/or causes of a particular disease, disorder, and/or condition (e.g., cancer). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

DETAILED DESCRIPTION OF CERTAIN EMBODIMENTS

The following description is for illustration and exemplification of the invention only and is not intended to limit the invention to the specific embodiments described.

Unless defined otherwise, technical and scientific terms have the same meaning as commonly understood by one of ordinary skill in the art to which this invention belongs.

All references cited herein, including patent applications and publications, are incorporated by reference in their entirety.

As mentioned above, the present invention relates to novel pharmaceutical compositions and/or methodologies for treating certain dopamine-related diseases, disorders and conditions. In many embodiments, the present invention relates to compositions and/or methodologies for treating neurodegenerative diseases (e.g., Parkinson's Disease), in the following frequently referred to as PD). In particular, the present invention relates to intra-intestinal (typically duodenal or jejunal) administration of dopamine replacement agents, a COMT inhibitor (e.g., entacapone, opicapone, tolcapone, etc., and combinations thereof), together with a dopamine replacement agent (e.g., levodopa, melevodopa, etilevodopa, budipine and combinations thereof) and a dopamine decarboxylase inhibitor (e.g., carbidopa, benserazide, and combinations thereof), in the context of a pharmaceutical composition that is characterized by being in gel form. In many embodiments, all three components are administered intra-intestinally, and often in the same composition (i.e., in the same unit dosage form).

Dopamine-Related Diseases, Disorders, and Conditions

In many embodiments, the present disclosure relates to treatment of one or more dopamine-related diseases, disorders, or conditions. In some embodiments, the present disclosure particularly relates to treatment of levodopa-responsive patients.

As noted above, dopamine is a neurotransmitter. Dopamine plays a number of important roles in the nervous system, and several important diseases, disorders and conditions are associated with dysfunction in the dopamine system. In some embodiments, a dopamine-related disease, disorder or condition may be associated with and altered level and/or activity of dopamine in one or more relevant nervous system areas or tissues (e.g., in the brain or a particular region thereof) relative to that observed absent the disease, disorder or condition. In many embodiments, such an altered level is a decreased level.

Exemplary dopamine-related diseases, disorders and conditions may include albinism, Alzheimer's disease, amblyopia, angelman syndrome, anterior ischemic optic neuropathy, aphasia, back pain, depression, dopamine beta-hydroxylase deficiency, drug (e.g., alcohol, cocaine, opiate) dependence/abuse, dyslexia, dystonic cerebral palsy, Huntington's disease, hypotensive syncope, impulse control disorder, medullary carcinoma, motor neuron disease, movement disorders, multisystemic atrophy, orthostatic hypotension, orthostatic intolerance, Parkinson's disease, prion disease, restless legs syndrome, retinal diseases, schizophrenia, spinal cord injury, spinal muscular atrophy, spinocerebellar ataxia, stroke, thyroid carcinoma, thyroid neoplasm, tourette syndrome, etc.

In some embodiments, dopamine-related disease, disorder or conditions may be or comprise one or more proliferative disorders (e.g., cancers), inflammatory conditions, neurodegenerative diseases, etc., and combinations thereof.

In many embodiments, dopamine-related diseases, disorders or conditions are neurodegenerative disorders (e.g., PD, AD, HD).

Embodiments of the present disclosure are particularly relevant for treatment of PD. In general, a patient to which therapy as described herein is administered may be in any phase of PD. In many embodiments, however, a PD patient is in a moderate to advanced phase, for example consistent with Hoehn and Yahr (H&Y) stage II or higher. In some embodiments, a PD patient is experiencing motor fluctuations and hyper-/dyskinesia. In some embodiments, a PD patient has received prior therapy with one or more conventional treatments as described herein (e.g., that involve intermittent dosing and/or patient exposure to active agent(s)). In some particular embodiments, a PD patient may have received prior oral levodopa therapy and be experiencing motor fluctuations. In some embodiments, the present disclosure proposes that such motor fluctuations may result, at least to some extent, from pulsatile dopaminergic stimulation, in some situations compounded by short half-life and/or erratic absorption (e.g., as can result from gastric emptying) of oral levodopa therapy. In some aspects, the present disclosure provides the insight that certain compositions provided herein (including specifically certain gel compositions for intra-intestinal administration that include as active agents each of (a) a dopamine replacement agent; (b) a DDI; and (c) a COMT inhibitor) can provide various advantages in the treatment of such patients. Without wishing to be bound by any particular theory, it is proposed that such compositions may achieve substantially continuous dopaminergic stimulation in these (and other) patients, thereby improving therapeutic outcome and, in particular, reducing risk of developing or worsening motor fluctuations.

The patient can be treated with some few tablets per day but is typically receiving a cocktail of anti-Parkinson medications. The patient can also be treated with a more continuous dopaminergic stimulation such as Levodopa Carbidopa Intestinal Gel (DUODOPA®, DUOPA®), Apomorphine, DBS and/or patch or a combination thereof.

Current recommended therapy for dopamine-related diseases, disorder, and conditions often includes administration of dopamine, of a precursor compound (e.g., levodopa, melevodopa, etilevodopa) that is metabolically converted to dopamine after administration, or of another type of dopamine replacement agent. In particular, the metabolic precursor levodopa is commonly administered in the treatment neurodegenerative dopamine-related diseases, disorders or conditions, particularly such as PD.

Dopamine Replacement Agents

As noted above, many dopamine-related diseases, disorders and conditions are associated with decreased dopamine levels in one or more relevant tissues or sites. Recommended therapy often includes administration of dopamine, or of a precursor compound that is metabolically converted to dopamine after administration. In particular, given that dopamine does not cross the blood-brain barrier, alternative agents that do are particularly desirable for treatment of neurodegenerative dopamine-related diseases, disorders or conditions, particularly such as PD. Such agents are referred to herein as "dopamine replacement agents" and include, for example, metabolic precursors of dopamine (e.g., levodopa, melevodopa, etilevodopa, etc. and combinations thereof), dopamine agonists (e.g., apomorphine, bromocriptine, cabergoline, dihydroergocristine mesylate, pergolide, piribedil pramipexole, ropinirole, rotigotine, etc. and combinations thereof), agents that block dopamine degradation (e.g., MAO-B inhibitors such as selegiline, rasagiline, etc., and combinations thereof) and/or agents (e.g., budipine) that otherwise stimulate dopamine production. Various commercial formulations and preparations of such agents are known in the art, including certain oral (e.g., capsule or tablet), transdermal (e.g., patch), parenteral (e.g., subcutaneous, intravenous, intrathecal, etc., particularly for infusion), and/or other (e.g., gel, and particularly intra-intestinal gel) formulations.

Levodopa therapy is currently standard of care for treatment of PD.

Levodopa, an aromatic amino acid, is a white, crystalline compound, slightly soluble in water, with a molecular weight of 197.2. It is designated chemically as (−)-L-α-amino-β-(3,4-dihydroxybenzene) propanoic acid. Its empirical formula is $C_9H_{11}NO_4$ and its structural formula is:

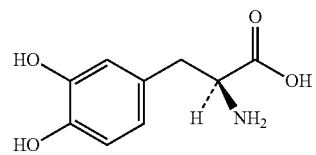 [SMILES: N[C@@H](Cc1ccc(O)c(O)c1)C(=O)O]

Levodopa is a metabolic precursor not only to dopamine, but also to other neurotransmitters such as norepinephrine (noradrenaline) and epinephrine (adrenaline), both of which are, like dopamine, members of the catecholamine class.

Levodopa dosing and administration, particularly to subjects suffering from PD, can present challenges. Before individuals develop clinical symptoms of PD, they will already have lost 50 to 60% of the dopamine neurons in the brain, resulting in a corresponding reduction of approximately 70 to 80% in dopamine concentration. In early disease, surviving neurons are still able to take up levodopa, store it as dopamine, and slowly release it over time in a continuous and relatively constant fashion despite fluctuating plasma levodopa levels due to the short half-life of levodopa and the frequently unpredictable intestinal absorption of the oral medicament. With progressive disease, however, more dopamine neurons die and this buffering capacity is lost.

With time patients therefore begin to notice that the beneficial effects of levodopa last a few hours and then diminish or wear off, a phenomenon known as motor fluctuations. As more dopamine neurons are lost, a patient's clinical response will more closely mirror fluctuations in blood levodopa concentrations, and eventually the levodopa response may last only 1 or 2 hours to then wear off Due to the loss of the buffering capacity, the dopamine receptors will be exposed to fluctuating dopamine concentrations resulting from fluctuating plasma levodopa levels. When the levodopa-derived dopamine concentration in the brain is too high, the patient experiences dyskinesias (turning movements), and when the brain dopamine concentration is too low, PD symptoms return. This creates a therapeutic window that progressively narrows over time. Once a patient exhibits dyskinesias, the addition of more dopamine medication will increase dyskinesias, whereas a reduction in dopamine medication will increase the off time, where PD symptoms return.

The pulsatile dopamine stimulation obtained with oral levodopa formulations is only somewhat reduced with traditional sustained release oral levodopa formulations. Alternative formulations and dosing strategies continue to be explored in hopes of improving effective levodopa administration. The present disclosure provides technologies for achieving improved levodopa administration, in particular in combination with a DDI and a COMT inhibitor, specifically by providing compositions and methods that achieve controlled exposure to each of these agents with surprising benefit to the subject. Additionally, in some embodiments, the present disclosure provides combination compositions (e.g., compositions that include each of levodopa, a DDI, and a COMT inhibitor [particularly entacapone]) that, as demonstrated herein, surprisingly improve levodopa stability, in some embodiments even as compared with alternative formulations of the same three agents.

In some embodiments, in accordance with the present invention, levodopa may be administered orally. In some embodiments, in accordance with the present invention, levodopa may be administered intra-intestinally.

In some embodiments, in accordance with the present invention, levodopa may be administered in a tablet format. In some embodiments, in accordance with the present invention, levodopa may be administered in a gel format. In some particular embodiments, levodopa may be administered intra-intestinally in a gel format.

Various formats for administration of levodopa, and compositions thereof, are known in the art. Some such compositions include particular inhibitors of enzymes associated with the metabolic degradation of levodopa. For example, PARCOPA® tablets contain both levodopa and carbidopa, and are characterized by rapid disintegration on the tongue that does not require water to aid dissolution or swallowing; SINEMET® and SINEMET® CR are sustained-release tablets containing levodopa and carbidopa; KINSON® tablets contain both levodopa and carbidopa; MADOPAR® tablets contain levodopa and benserazide hydrochloride; and STALEVO® are tablets containing levodopa, carbidopa and entacapone.

Additionally, DUODOPA® is an intestinal gel containing a combination of levodopa and carbidopa in a ratio of 4 to 1 that is described as providing continuous intestinal infusion of levodopa. Use of this gel format has been reported to reduce motor fluctuations and increase "on" time for patients (e.g., with advanced PD), relative to that observed with oral formulations. It is believed that motor fluctuations and hyper-diskinesias are reduced in patients receiving DUODOPA® (relative to those receiving oral therapy) because the plasma concentrations of levodopa are kept at a steady level within a therapeutic window. DUODOPA® is administered via an inserted tube directly into the duodenum. Levodopa is absorbed quickly and effectively from the intestine through a high capacity transport system for amino acids. Levodopa has the same bioavailability (81-98%) when administered via the DUODOPA® gel as when administered in a tablet. However, variation in plasma levodopa/dopamine concentration within an individual is considerably smaller when levodopa is administered via the DUODOPA® gel (as compared with via a tablet); it has been proposed that such reduced variation may be attributable to continuous intestinal administration in achieved by DUODOPA® gel, which avoids influence of gastric emptying rate on absorption rate. With an initial high morning dose of DUODOPA® intestinal gel, the therapeutic plasma level of levodopa/dopamine is reached within 10-30 minutes.

Particular available pharmaceutical compositions of levodopa, including STALEVO® tablets, are described in, for example, U.S. Pat. Nos. 6,500,867 B1 and 6,797,732 B2. Oral pharmaceutical compositions comprising levodopa, carbidopa and entacapone are disclosed in WO 2008/053297, WO 2012/147099, US 2006/0222703, and WO 2009/098661. Certain gel compositions of levodopa, and in particular intra-intestinal gel formats such as DUODOPA® are described, for example, in U.S. Pat. No. 5,635,213 and EP 0670713 B1.

Prescribing information for PARCOPA® indicates that it is supplied in three strengths: PARCOPA® 25/100, containing 25 mg of carbidopa and 100 mg of levodopa; PARCOPA® 10/100, containing 10 mg of carbidopa and 100 mg of levodopa; and PARCOPA® 25/250, containing 25 mg of carbidopa and 250 mg of levodopa. Inactive ingredients are aspartame, citric acid, crospovidone, magnesium stearate, mannitol, microcrystalline cellulose, natural and artificial mint flavor and sodium bicarbonate. PARCOPA® 10/100 and 25/250 also contain FD&C blue #2 HT aluminum lake. PARCOPA® 25/100 also contains yellow 10 iron oxide. PARCOPA® is indicated in the treatment of the symptoms of idiopathic Parkinson's disease (paralysis agitans), post-encephalitic parkinsonism, and symptomatic parkinsonism which may follow injury to the nervous system by carbon monoxide intoxication and/or manganese intoxication. PARCOPA® is indicated in these conditions to permit the administration of lower doses of levodopa with reduced nausea and vomiting, with more rapid dosage titration, with a somewhat smoother response, and with supplemental pyridoxine (vitamin B6). Recommended dosing involves initiation with one tablet of PARCOPA® 25/100 three times a day. This dosage schedule provides 75 mg of carbidopa per day. Dosage may be increased by one tablet every day or every other day, as necessary, until a dosage of eight tablets of PARCOPA® 25/100 a day is reached. If PARCOPA® 10/100 is used, dosage may be initiated with one tablet three or four times a day. However, this will not provide an adequate amount of carbidopa for many patients. Dosage may be increased by one tablet every day or every other day until a total of eight tablets (2 tablets q.i.d.) is reached.

Prescribing information provided with SINEMET® tablets describes them as "a combination of carbidopa and levodopa" and indicates for "the treatment of Parkinson's disease". SINEMET® tablets contain 25 mg of carbidopa and 100 mg of levodopa, and are dosed three times a day. Dosage may be increased by one tablet every day or every other day, as necessary, to a maximum daily dose of eight tablets. SINEMET® should not be administered to a subject otherwise exposed to levodopa; SINEMET® dosing should not be initiated until at least twelve hours after other administration of levodopa has been discontinued.

Prescribing information for KINSON® tablets indicates that they contain 100 mg of levodopa and 25 mg of anhydrous cabidopa. The tablets also contain the following inactive ingredients: cellulose-microcrystalline, starch-maize, sodium starch glycollate, talc-purified, povidone, magnesium stearate, quinoline yellow CI 47005. KINSON® tablets are approved for the treatment of PD and Parkinson's syndrome. They are said to be useful in relieving many of the symptoms of Parkinsonism, particularly rigidity and bradykinesia, and are also reported to frequently be helpful in the management of tremor, dysphagia, sialorrhoea, and postural instability associated with Parkinson's disease and syndrome. As with many other levodopa/carbidopa combination products, KINSON® is not recommended for administration to patients receiving other levodopa therapy; levodopa administration should be discontinued at least 12 hours prior to initiation of therapy with KINSON®. Titrated dosing is recommended, so that dose is tailored to each individual patient, though it is noted that peripheral dopamine decarboxylase is saturated by carbidopa at approximately 70-100 mg per day and that patients receiving less than this amount are more likely to experience nausea and vomiting.

According to its prescribing information, MADOPAR® is described as "a medicine used in Parkinson's disease" that contains "benserazide hydrochloride/levodopa". MADOPAR® tablets contain 50 mg of levodopa and 12.5 mg of benserazide hydrochloride; recommended dosing is four to eight capsules a day.

Prescribing information provided with STALEVO® tablets describes them as "combination of carbidopa, levodopa and entacapone" and indicates they are for use in "the treatment of Parkinson's disease". STALEVO® tablets contain 50 mg of carbidopa, 200 mg of levodopa and 200 mg of entacapone; maximum recommended dosing is six tablets within a 24-hour period.

Prescribing information provided with DUOPOPA® indicates that the gel contains 20 mg of levodopa and 5 mg of carbidopa monohydrate per 1 mL of gel. Inactive ingredients include carmellose sodium and water purified. DUOPOPA® is approved in the United States for the treatment of advanced idiopathic Parkinson's disease with severe motor fluctuations despite optimized oral treatment. It is recommended that a positive clinical response to DUOPOPA® administered via a temporary nasoduodenal tube be confirmed before a permanent percutaneous endoscopic gastrostomy (PEG) tube is inserted. DUOPOPA® also may be delivered directly to patient's small intestine. DUOPOPA® is intended for continuous daytime intestinal administration. Administration with a portable pump (specifically, the CADD-legacy DUOPOPA® pump (CE 0473)) directly into the duodenum by a permanent tube via percutaneous endoscopic gastrostomy (PEG) with an outer transabdominal tube and an inner intestinal tube is recommended, particularly for long term administration. Alternatively a radiological gastrojejunostomy may be considered if PEG is not suitable for any reason. It is recommended that a temporary nasoduodenal tube be used to find out if the patient responds favourably to this method of treatment and to adjust the dose before treatment with a permanent tube is started. Dose is typically adjusted to an optimal clinical response for the individual patient, which means maximizing the functional ON-time during the day by minimizing the number of OFF episodes and the time OFF (bradykinesia) and minimizing ON-time with disabling dyskinesia. It is recommended that, at least initially, DUOPOPA® be given initially as monotherapy (i.e., administered to a subject not simultaneously receiving other therapy).

In some embodiments, the present disclosure provides and/or utilizes a pharmaceutical gel composition for intra-intestinal administration of levodopa. In some embodiments, such a composition comprises about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, about 75 mg/ml, about 80 mg/ml, about 85 mg/ml, about 90 mg/ml, about 95 mg/ml, about 100 mg/ml, about 105 mg/ml, about 110 mg/ml, about 115 mg/ml, about 120 mg/ml, about 125 mg/ml, about 130 mg/ml, about 135 mg/ml, about 140 mg/ml, about 145 mg/ml, or about 150 mg/ml of levodopa. In some embodiments, such a composition comprises about, 10 mg/ml to about 150 mg/ml, 10 mg/ml to about 140 mg/ml, 10 mg/ml to about 130 mg/ml, 10 mg/ml to about 120 mg/ml, 10 mg/ml to about 110 mg/ml, 10 mg/ml to about 100 mg/ml, about 10 mg/ml to about 90 mg/ml, about 10 mg/ml to about 85 mg/ml, about 10 mg/ml to about 80 mg/ml, about 10 mg/ml to about 75 mg/ml, about 10 mg/ml to about 70 mg/ml, about 10 mg/ml to about 65 mg/ml, about 10 mg/ml to about 60 mg/ml, about 10 mg/ml to about 55 mg/ml, about 10 mg/ml to about 50 mg/ml, or about 20 mg/ml to about 50 mg/ml, of levodopa.

In some embodiments, the present disclosure may provide or utilize a pharmaceutical composition for oral administration of levodopa. In some embodiments, such a composition comprises about 50 mg, about 75 mg, about 100 mg, about 125 mg, about 150 mg, about 175 mg, about 200 mg, about 225 mg, about 250 mg, about 275 mg, or about 300 mg of levodopa.

Dopamine Decarboxylase Inhibitor (DDI)

Levodopa has a short half-life in the body, 30 to 60 minutes, and upon intake of levodopa alone, more than 90% is metabolized to dopamine before levodopa reaches the brain. Thus, many protocols for administering levodopa involve administration of large doses, which then lead to high extracerebral concentrations of dopamine that may often be accompanied by nausea and other adverse side-effects. To increase the bioavailability of levodopa, and reduce its side-effects, levodopa is therefore usually administered concurrently with a dopamine decarboxylase inhibitor (DDI), typically carbidopa (L-2-hydrazino-3-(3,4-dihydroxyphenyl)-2-methylpropanoic acid) or benserazide (DL-2'-(2,3,4-trihydroxybenzyl) serine hydrazide), which inhibits the conversion of levodopa to dopamine outside the brain, and which does not cross the blood-brain barrier.

Carbidopa

Carbidopa, an inhibitor of aromatic amino acid decarboxylation, is a white, crystalline compound, slightly soluble in water, with a molecular weight of 244.2. It is designated chemically as (−)-L-α-hydrazino-α-methyl-β-(3,4-dihydroxybenzene) propanoic acid monohydrate.

Carbidopa often exists and/or is utilized in monohydrate form, which has a molecular weight of 226.3. Its empirical formula is $C_{10}H_{14}N_2O_4 \times H_2O$, and its structural formula is:

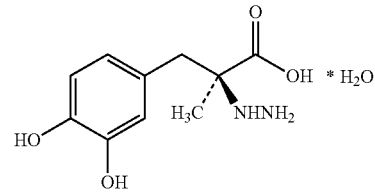 [SMILES: C[C@@](Cc1ccc(O)c(O)c1)(NN)C(=O)O]

In many embodiments, reference to an amount of carbidopa by weight or weight percent may be understood as the amount found in that weight (or weight percent) of carbidopa monohydrate (i.e., may be or be understood as an amount equivalent to the recited weight of carbidopa monohydrate).

Carbidopa is available in a variety of formats for administration to patients. For example, carbidopa is marketed as an oral tablet under the name Lodosyn. Lodosyn tablets contain 25 mg of carbidopa and are indicated for use with carbidopa-levodopa or with levodopa in the treatment of the symptoms of idiopathic Parkinson's disease (paralysis agitans), postencephalitic parkinsonism, and symptomatic parkinsonism, which may follow injury to the nervous system by carbon monoxide intoxication and/or manganese intoxication. In particular, Lodosyn is for use with carbidopa-levodopa in patients for whom the dosage of carbidopa-levodopa provides less than adequate daily dosage (usually 70 mg daily) of carbidopa. Lodosyn is particularly said to be for use with levodopa in the occasional patient whose dosage requirement of carbidopa and levodopa necessitates separate titration of each medication. It has been reported that use of Lodosyn with carbidopa-levodopa or with levodopa to permit the administration of lower doses of levodopa with reduced nausea and vomiting, more rapid dosage titration, and with a somewhat smoother response that that otherwise observed with administration of the relevant format/regimen of levodopa. However, it is noted that patients with markedly irregular ("on-off") responses to levodopa have not been shown to benefit from the addition of carbidopa. Lodosyn should be dosed by titration. Most patients are said to respond to a 1:10 proportion of carbidopa and levodopa, provided the daily dosage of carbidopa is 70 mg or more a day. The maximum daily dosage that should be administered to subjects receiving Lodosyn (whether as the only source of carbidopa or in combination with a levodopa/carbidopa product) should not exceed 200 mg.

As discussed above, carbidopa is also available in certain formats in which it is provided in combination with levodopa (e.g., oral formats and intra-intestinal gel formats).

In some embodiments, the present disclosure provides and/or utilizes a pharmaceutical gel composition (e.g., for intra-intestinal administration) comprising a pharmaceutically active agent that comprises or consists of carbidopa. In some embodiments, the present disclosure provides and/or utilizes a pharmaceutical gel composition. In certain embodiments, the present disclosure provides a gel composition (e.g., for intra-intestinal administration) comprising a pharmaceutically active agent that comprises or consists of carbidopa in combination with a dopamine replacement agent (e.g., levodopa), a COMT inhibitor (e.g., entacapone), or both.

In some embodiments, the present disclosure provides and/or utilizes a gel composition (e.g., for intra-intestinal administration) that comprises about 0.5 mg/ml, about 1.0 mg/ml, about 1.5 mg/ml, about 2.0 mg/mg, 2.5 mg/ml, about 3.0 mg/mg, about 3.5 mg/mg, about 4.0 mg/mg, about 4.5 mg/mg, about 5 mg/ml, about 5.5 mg/mg, about 6.0 mg/mg, about 6.5 mg/mg, about 7.0 mg/mg, about 7.5 mg/ml, about 8.0 mg/mg, about 8.5 mg/mg, about 9.0 mg/mg, about 9.5 mg/mg, about 10 mg/ml, about 12.5 mg/ml, about 15 mg/ml, about 17.5 mg/ml, or about 20 mg/ml of carbidopa. In some embodiments, such a composition comprises about 2.5 mg/ml to about 25 mg/ml, about 2.5 mg/ml to 22.5 mg/ml, about 2.5 mg/ml to about 20 mg/ml, about 2.5 mg/ml to about 17.5 mg/ml, about 2.5 mg/ml to about 15 mg/ml, about 2.5 mg/ml to about 12.5 mg/ml, or about 2.5 mg/ml to about 10 mg/ml of carbidopa.

Benserazide

Benserazide is an inhibitor of aromatic amino acid decarboxylation with a molecular weight of 257.2. It is designated chemically as (RS)-2-amino-3-hydroxy-N'-(2,3,4-trihydroxybenzyl)propanehydrazide. Its empirical formula is $C_{10}H_{15}N_3O_5$ and its structural formula is:

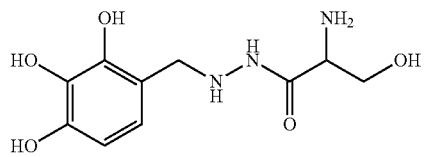 [SMILES: NC(CO)C(=O)NNCc1ccc(O)c(O)c1O]

As noted above, benserazide is included in certain commercially available pharmaceutical products, and particularly in combination products (specifically MADOPAR®, discussed above, which is also marketed as PROLOPA® in certain jurisdictions) with levodopa.

In some embodiments, the present invention may utilize one or more available pharmaceutical products containing benserazide. In certain embodiments, however, the present disclosure provides and/or utilizes benserazide in a novel gel composition. In certain embodiments, the present disclosure contemplates intra-intestinal administration of benserazide, for example via an intra-intestinal gel. In some embodiments, the present disclosure provides a gel composition (e.g., for intra-intestinal administration) comprising a pharmaceutically active agent that comprises or consists of benserazide. In certain embodiments, the present disclosure provides a gel composition (e.g., for intra-intestinal administration) comprising a pharmaceutically active agent that comprises or consists of benserazide in combination with a dopamine replacement agent (e.g., levodopa), a COMT inhibitor (e.g., entacapone), or both.

In some embodiments, the present disclosure provides and/or utilizes a pharmaceutical gel composition for intra-intestinal administration of benserazide. In some embodiments, such a composition comprises about 2.5 mg/ml, about 5.0 mg/ml, about 7.5 mg/ml, about 10 mg/ml, about 12.5 mg/ml, about 15 mg/ml, about 17.5 mg/ml, or about 20 mg/ml of benserazide. In some embodiments, such a composition comprises about 2.5 mg/ml to about 25 mg/ml, about 2.5 mg/ml to 22.5 mg/ml, about 2.5 mg/ml to about 20 mg/ml, about 2.5 mg/ml to about 17.5 mg/ml, about 2.5 mg/ml to about 15 mg/ml, about 2.5 mg/ml to about 12.5 mg/ml, or about 2.5 mg/ml to about 10 mg/ml of benserazide.

In some embodiments, the present disclosure provides and/or utilizes a pharmaceutical gel composition for intra-intestinal administration of dopamine decarboxylase inhibitors. In some embodiments, such a comprises about 2.5 mg/ml, about 5.0 mg/ml, about 7.5 mg/ml, about 10 mg/ml, about 12.5 mg/ml, about 15 mg/ml, about 17.5 mg/ml, or about 20 mg/ml of one or more dopamine decarboxylase inhibitors. In some embodiments, such a composition comprises about 2.5 mg/ml to about 25 mg/ml, about 2.5 mg/ml to 22.5 mg/ml, about 2.5 mg/ml to about 20 mg/ml, about 2.5 mg/ml to about 17.5 mg/ml, about 2.5 mg/ml to about 15 mg/ml, about 2.5 mg/ml to about 12.5 mg/ml, or about 2.5 mg/ml to about 10.0 mg/ml of one or more dopamine decarboxylase inhibitors.

In some embodiments, the present disclosure may provide or utilize a pharmaceutical composition for oral administration of DDIs. In some composition comprises about 12.5 mg to about 75 mg of one or more DDIs.

Catechol-O-Methyltransferase (COMT) Inhibitor

In some embodiments, features of the present invention include recognition that certain beneficial effects may be achieved and/or problems avoided through administration of a COMT inhibitor in a gel composition, and particularly in an intra-intestinal gel composition, optionally in combination with one or more other active agents (e.g., with levodopa and/or with a DDI). The present disclosure demonstrates, for example, that intra-intestinal administration of a COMT inhibitor in a pharmaceutical gel composition has particular benefit for subjects receiving therapy with a dopamine precursor, and particularly with levodopa.

In some embodiments, such administration permits reduced exposure of the subjects to levodopa relative to that required with other formats and/or regimens for administration of levodopa (e.g., alone, in combination with a DDI (e.g., carbidopa), and/or in a different format).

Alternatively or additionally, such administration can reduce negative effects (e.g., hydrazine level) in subjects receiving therapy with levodopa and DDI (e.g., carbidopa). Still further, the present disclosure specifically demonstrates improved storage stability characteristics for certain gel compositions when a COMT inhibitor (e.g., entacapone) is included in the composition.

In some aspects, the present disclosure establishes such improved storage stability characteristics for pharmaceutical gel compositions that contain levodopa and carbidopa; that is, the present disclosure demonstrates such improved storage stability characteristics when a COMT inhibitor (e.g., entacapone) is included in a gel composition comprising levodopa and carbidopa as compared with an otherwise comparable composition lacking the COMT inhibitor. As will be understood by those skilled in the art reading the present disclosure, the findings exemplified herein may reasonably be generalized to other combinations of COMT inhibitors, DDI inhibitors and/or dopamine precursors.

Still further, the present disclosure documents a surprising feature of certain gel compositions comprising a dopamine precursor (e.g., levodopa), a DDI (e.g., carbidopa), and a COMT inhibitor (e.g., entacapone) in that intra-intestinal administration of such compositions enhance bioavailability of the dopamine precursor to an extent greater than observed with comparable combinations in other formats.

In patients with PD, levodopa may after peripheral administration also be directly metabolized by the enzyme catechol-O-methyltransferase (COMT) to 3-O-methyldopa (3-OMD; 3-methoxy-4-hydroxy-L-phenylalanine). In order to further increase the levodopa half-life in the body, a catechol-O-methyltransferase inhibitor, typically entacapone ((2E)-2-cyano-3-(3,4-dihydroxy-5-nitrophenyl)-N,N-diethyl-prop-2-enamide), has been administered in conjunction with levodopa and carbidopa. Entacapone as a catechol-O-methyltransferase (COMT) inhibitor is described in the European patent No. 0444899 B1. Another COMT inhibitor used as an adjunct to levodopa/carbidopa medication is tolcapone (3-dihydroxy-4'-methyl-5-nitrobenzophenone). A recently developed COMT inhibitor for add-on therapy to levodopa is opicapone (2,5-dichloro-3-[5-(3,4-dihydroxy-5-nitrophenyl]-1,2,4-oxadiazol-3-yl)-4,6-dimethylpyridine-1-oxide).

Entacapone, an inhibitor of catechol-O-methyltransferase (COMT), is a nitro-catechol-structured compound with a molecular weight of 305.3. The chemical name of entacapone is (E)-2-cyano-3-(3,4-dihydroxy-5-nitrophenyl)-N,N-diethyl-2-propenamide. Its empirical formula is $C_{14}H_{15}N_3O_5$ and its structural formula is:

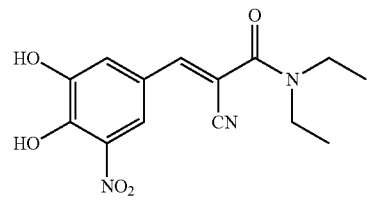 [SMILES: CCN(CC)C(=O)/C(C#N)=C/c1cc(O)c(O)c([N+](=O)[O-])c1]

In some embodiments, the present disclosure provides and/or utilizes a pharmaceutical gel composition for intra-intestinal administration of entacapone. In some embodiments, such a composition comprises about 5.0 mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, or about 75 mg/ml of entacapone. In some embodiments, such a composition comprises about 5.0 mg/ml to about 100 mg/ml, about 5.0 mg/ml to about 90 mg/ml, about 5.0 mg/ml to about 85 mg/ml, about 5.0 mg/ml to about 80 mg/ml, about 5.0 mg/ml to about 75 mg/ml, about 5.0 mg/ml to about 70 mg/ml, about 5.0 mg/ml to about 65 mg/ml, about 5.0 mg/ml to about 60 mg/ml, about 5.0 mg/ml to about 55 mg/ml, about 5.0 mg/ml to about 50 mg/ml, about 5.0 mg to about 45 mg/ml, about 5.0 mg/ml to about 40 mg/ml of entacapone.

In some embodiments, the present disclosure may provide or utilize a pharmaceutical composition for oral administration of entacapone. In some embodiments, such a composition comprises about 12.5 mg to about 250 mg of entacapone.

Opicapone is an inhibitor of catechol-O-methyltransferase (COMT) with a molecular weight of 413.17. The chemical name of opicapone is (4Z)-4-[3-(2,5-dichloro-4,6-dimethyl-1-oxidopyridin-1-ium-3-yl)-2H-1,2,4-oxadiazol-5-ylidene]-2-hydroxy-6-nitrocyclohexa-2,5-dien-1-one. Its empirical formula is $C_{15}H_{10}Cl_2N_4O_6$ and its structural formula is

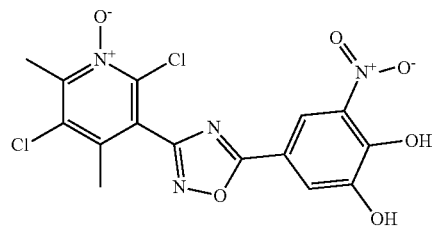 [SMILES: Cc1c(Cl)c(C)[n+]([O-])c(Cl)c1-c1noc(-c2cc(O)c(O)c([N+](=O)[O-])c2)n1]

In some embodiments, the present disclosure provides and/or utilizes a pharmaceutical gel composition for intra-intestinal administration of opicapone. In some embodiment, such a composition comprises about 0.5 mg/ml, about 1.0 mg/ml, about 1.5 mg/ml, about 2.0 mg/ml, about 2.5 mg/ml, about 3.0 mg/ml, about 4.0 mg/ml, about 5.0 mg/ml, about 6.0 mg/ml, about 7.0 mg/ml, about 8.0 mg/ml, about 9.0 mg/ml, or about 10 mg/ml of opicapone. In some embodiments, such a composition comprises about 0.5 mg/ml to about 10 mg/ml, about 0.5 mg/ml to about 9.0 mg/ml, about 0.5 mg/ml to about 8.5 mg/ml, about 0.5 mg/ml to about 8.0 mg/ml, about 0.5 mg/ml to about 7.5 mg/ml, about 0.5 mg/ml to about 7.0 mg/ml, about 0.5 mg/ml to about 6.5 mg/ml, about 0.5 mg/ml to about 6.0 mg/ml, about 0.5 mg/ml to about 5.5 mg/ml, or about 0.5 mg/ml to about 5.0 mg/ml of opicapone.

In some embodiments, the present disclosure may provide or utilize a pharmaceutical composition for oral administration of opicapone. In some embodiments, such a composition comprises about 10 mg to about 100 mg of opicapone.

Tolcapone is an inhibitor of catechol-O-methyltransferase (COMT) with a molecular weight of 273.2. The chemical name of opicapone is (3,4-Dihydroxy-5-nitrophenyl)(4-methylphenyl)methanone. Its empirical formula is $C_{14}H_{11}NO_5$ and its structural formula is

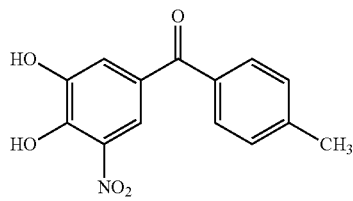 [SMILES: Cc1ccc(C(=O)c2cc(O)c(O)c([N+](=O)[O-])c2)cc1]

In some embodiments, the present disclosure provides and/or utilizes a pharmaceutical gel composition for intra-intestinal administration of tolcapone. In some embodiments, such a composition comprises about 5.0 mg/ml about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, or about 75 mg/ml of tolcapone. In some embodiments, such a composition comprises about 10 mg/ml to about 100 mg/ml, about 10 mg/ml to about 90 mg/ml, about 10 mg/ml to about 85 mg/ml, about 10 mg/ml to about 80 mg/ml, about 10 mg/ml to about 75 mg/ml, about 10 mg/ml to about 70 mg/ml, about 10 mg/ml to about 65 mg/ml, about 10 mg/ml to about 60 mg/ml, about 10 mg/ml to about 55 mg/ml, about 10 mg/ml to about 50 mg/ml, or about 5.0 mg/ml to about 40 mg/ml of tolcapone.

In some embodiments, the present disclosure may provide or utilize a pharmaceutical composition for oral administration of tolcapone. In some embodiments, such a composition comprises about 12 mg to about 75 mg of tolcapone.

Intra-Intestinal Compositions

Certain attempts have been made to improve stability of levodopa in pharmaceutical compositions and/or to improve consistency of its delivery, for example in hopes of reducing one or more side effects (e.g., dyskinesias) of levodopa administration and/or reducing frequency and/or length of "off periods".

For example, as discussed above, infusion technologies have been developed (particularly for treatment of for late stage PD patients), according to which levodopa is continuously administered through infusion via an external pump and directly into the part of the small intestine (e.g., duodenum or jejunum) where most of the levodopa is absorbed. Such an approach is believed to provide more continuous plasma levels, which in turn are intended to achieve reduction in both off periods and dyskinesias. It is also known that continuous delivery can reduce motor complications, as such complications are due to non-physiological, and intermittent administration of the drug. (Olanow et al, www.thelancet.com/neurology, Vol 13, P 141-149, 2014) However, due to the low aqueous solubility of levodopa and carbidopa, large volumes of levodopa/carbidopa solutions had to be used which were cumbersome and impractical to the patient.

Other technologies that have been developed include, for example, a liquid composition of levodopa and carbidopa which is stabilized by citric acid and EDTA, as described in EP 1670450 B1.

Furthermore, as discussed above, an intra-intestinal gel technology has been developed in which micronized levodopa and carbidopa are suspended in a methyl cellulose thickener gel, and the composition is delivered directly to the duodenum by intraduodenal infusion. Specifically, an intra-intestinal gel containing 20 mg/ml levodopa and 5 mg/ml carbidopa for intraduodenal infusion is marketed under the trade name DUODOPA®. Such pharmaceutical formulations for intraduodenal administration are disclosed in U.S. Pat. No. 5,635,213 and EP 0670713 B1. Long term 24 hours intestinal administration of levodopa/carbidopa is disclosed in WO 2007/138086 A1. DUODOPA® has been reported to display/achieve improvements in chemical stability of levodopa in an aqueous medium as compared with that observed for other levodopa formats. DUODOPA® has also been reported to have beneficial particle distribution (e.g., absence of sedimentation) characteristics, and to be useful in the treatment of PD.

The present disclosure provides certain compositions and therapeutic regimens that show improvements even relative to DUODOPA®. In some embodiments, for example, provided compositions (including specifically pharmaceutical gel compositions that, like DUODOPA®) include both levodopa and carbidopa further include a COMT inhibitor (e.g., entacapone). Thus, in some embodiments, the present disclosure provides gel compositions (e.g., for intra-intestinal administration) that comprise a pharmaceutically active agent that comprises or consists of a COMT inhibitor (e.g., entacapone) in combination with a dopamine replacement agent (e.g., levodopa), a DDI (e.g., carbidopa), or both.

Among other things, the present disclosure identifies the source of a problem with DUODOPA® as a pharmaceutical format for the storage and/or administration of levodopa. Specifically, the present disclosure appreciates that DUODOPA® has relatively short shelf-life (e.g., 15 weeks in refrigerator (e.g., 2-8° C.), 16 hours in room temperature (e.g., 25° C.)). DUODOPA® is even recommended to be stored frozen to extend its shelf-life. For example, one drug cassette can be only used up to 16 hours.

It has been reported that intraduodenal administration of DUODOPA® may sometimes be combined with oral administration of entacapone, which can increase bioavailability of levodopa. (https://.medicines.org.uk/emc/medicine/20786, last visited Sep. 3, 2015) However, the present disclosure identifies the source of a problem with such strategies, given that plasma drug level fluctuates due to unpredictable intestinal absorption of the oral medicament as discussed above. Thus, the present disclosure appreciates that it can be challenging to provide consistent result with the oral administration of entacapone, and therefore further appreciates that improved strategies for administration of a triple combination of levodopa, a DDI, and entacapone are desirable and can be developed.

A stable liquid composition that comprises levodopa, carbidopa and entacapone together with arginine and optionally meglumine for inter alia intraduodenal administration is disclosed in WO 2012/066538.

The present disclosure encompasses the insight that certain beneficial effects may be achieved by providing and utilizing certain gel compositions (e.g., for intra-intestinal administration) that comprise a COMT inhibitor (e.g., entacapone), and furthermore, that certain such gel compositions, e.g., wherein the pharmaceutically active agent included in the compositions comprises or consists of a combination of a dopamine replacement agent (e.g., levodopa), a DDI (e.g., carbidopa), and a COMT inhibitor (e.g., entacapone) have certain unexpected valuable properties as compared with other available formats including some or all of these agents. For example, among other things, the present disclosure demonstrates that provided three-agent gel compositions can provide stable plasma drug level and long shelf-life as compared with other formats.

In some embodiments, compositions provided by the present invention differ from the previously known levodopa/carbidopa intra-intestinal gel (in the following for brevity "LCIG"), such as DUODOPA®. Among other things, in some embodiments, provided compositions are characterized, for example, by improved stability of included active agents as compared with other compositions (e.g., DUODOPA®) including such agents. In some embodiments, provided compositions may contain and/or may be dosed so that a patient receives a lower or less frequent dose of one or more included active agents than is present in and/or occurs with other available compositions containing the agent(s).

In some particular embodiments, provided compositions are or include intra-intestinal gels and include levodopa, a DDI, and a COMT inhibitor. In some particular embodiments, provided compositions are intra-intestinal gel compositions that are substantially similar to one or more reference compositions described in one or more of intra-intestinal gels and/or marketed as DUODOPA®, but differ from such reference compositions in that they include a COMT inhibitor, such as entacapone, within them.

In comparison with an LCIG, inclusion of a COMT inhibitor (e.g., entacapone, opicapone, tolcapone) in accordance with certain embodiments of the present invention, may reduce the daily levodopa intake, by about 10-30%, thereby reducing the risk of the patient developing levodopa-related side effects, such as dyskinesia and motor fluctuation.

Reduction of the levodopa intake is also highly desirable. More severe neurographic abnormalities have been reported in patients treated with LCIG infusion than in orally treated patients. The degree of the severity of the neuropathic change correlating with increased dose of levodopa.

In some embodiments, administration of COMT inhibitors (e.g., entacapone, tolcapone) via the intra-intestinal gel composition may lead controlled entacapone or tolcapone delivery. In some embodiments, separate oral administration of entacapone or toplcapone may be combined with LCIG administration.

In some embodiments, the present disclosure may provide or utilize a pharmaceutical composition of DDIs and levodopa. In some embodiments, the weight ratio of DDIs to levodopa in such a composition is about 1:20 to about 1:2, about 1:15 to about 1:2, about 1:10 to about 1:2, about 1:8 to about 1:4, about 1:5 to about 1:3, about 1:15 to about 1:8, or about 1:12 to about 1:0. In some embodiments, the weight ratio of DDIs to levodopa in such a composition is about 1:12, about 1:11, about 1:10, about 1:9, about 1:8, about 1:7, about 1:6, about 1:5, about 1:4, about 1:3, or about 1:2.

In some embodiments, the present disclosure may provide or utilize a pharmaceutical composition of COMT inhibitors and levodopa. In some embodiments, the weight ratio of COMT inhibitors to levodopa in such a composition is about 10:1 to about 0.5:1, about 8:1 to about 4:1, about 5:1 to about 3:1, about 5:1 to about 0.5:1, about 3:1 to about 0.5:1, or about 2:1 to about 0.5:1. In some embodiments, the weight ratio of COMT inhibitors to levodopa in in such a composition is about 10:1, about 9:1, about 8:1, about 7:1, about 6:1, about 5:1, about 4:1, about 3:1, about 2:1, about 1:1, or about 0.5:1.

In some embodiments, a provided gel format is a semi-solid composition wherein the pharmaceutically active ingredients (e.g., levodopa, DDI and COMT inhibitor) are present in the form of particles suspended in an aqueous carrier having a viscosity of at least about 300 mPas, at a moderate shear rate, as defined herein.

In some embodiments, particles of active ingredients in an intra-intestinal gel composition may have a maximum particle size not exceeding about 80 µm, about 60 µm, about 40 µm, or about 20 µm. Particles may be micronized. Further, an aqueous carrier has a viscosity of at least 300 mPas, usually in the range of 300 to 5000 Pas, at a moderate shear rate (between 20 and 500 $s^{-1}$).

In some embodiments, a carrier may have plastic or pseudoplastic nature so that the viscosity will be lowered during agitation, whereby the liquid aqueous carrier will be easier to pump.

In some embodiments, an aqueous carrier is usually a dispersion or solution of a pharmaceutically acceptable colloid, a water-soluble or water-swellable colloid of polysaccharide type, including, for instance cellulose, methyl cellulose, ethyl cellulose, carboxymethyl cellulose and salts thereof, xanthan gum, carrageenan, or a synthetic polymer, e.g., polyvinylpyrrolidone or polyacrylic acid, combinations thereof.

In some embodiments, viscosity of a gel composition may be sufficiently high to carry drug load of active ingredients without a tendency of sedimentation. In some embodiments, viscosity may not be too high so that it should be possible to pump gel, for example, with an ambulatory pump (e.g., with reasonable battery consumption).

In certain embodiments, a suitable viscosity may be obtained by adjusting the molecular weight of colloid used into a suitable range, such as by adjusting the degree of polymerization. In some embodiments, the viscosity may be adjusted by selecting a suitable concentration of colloid in an aqueous system.

In some embodiments, viscosity of an intra-intestinal gel composition may be at least about 1800 mPas, or in the range of about 2200 to about 4500 mPas.

In some embodiments, intra-intestinal gel compositions further comprise other components. For example, in some embodiments, such compositions may comprise one or more pharmaceutically inactive components. In some embodiments, other components may be selected from the group consisting of metal chelators, preservatives, excipients, surfactants, emollients, buffers, and combinations thereof.

In some embodiments, intra-intestinal gel compositions further comprise or more dopamine agonists (e.g., bromocriptine, cabergoline, pergolide, pramipexole, ropinirole, rotigotine, apomorphine, dihydroergocristine mesylate, piribedil). Dopamine agonists activate dopamine receptors in the absence of dopamine, mimicking the functions of dopamine in the brain.

In some embodiment, intra-intestinal gel compositions further comprise one or more monoamine oxidase type B (MAO-B) inhibitors (e.g., rasagiline, selegiline). Monoamine oxidase type B (MAO-B) breaks down dopamine in the brain, catalyzing the oxidative deamination of biogenic and xenobiotic amines.

In some embodiment, intra-intestinal gel compositions further comprise one or more anticholinergics (e.g., antihistamines, tropine, tropine derivatives (e.g., ethers of tropine)). Anticholinergics block the binding acetylcholine to its receptor in nerve cells, therefore inhibits acetylcholine in nervous system.

In some embodiment, intra-intestinal gel compositions further comprise one or more glutamate antagonist.

In some embodiment, intra-intestinal gel compositions further comprise one or more amantadine or amantadine derivatives.

An intra-intestinal gel composition may be prepared by mixing a carrier with water to form a gel and then dispersing finely active components (e.g., levodopa, a DDI, and a COMT inhibitor) in the aqueous carrier using methods and apparatus which are well-known to those skilled in the art. The prepared formulations are then dispensed into suitable containers for intra-intestinal, such as duodenal, administration.

An intra-intestinal gel composition may be administered via intestinal administration (e.g., directly into the intestine (e.g., duodenum or jejunum)), by a direct jejunostomy, or via a percutaneous endoscopic gastrostomy.

In some embodiments, a gel is administered with a portable pump (e.g., peristaltic or syringe type). An exemplary peristaltic pump is that sold under the trade name CADD-Legacy DUODOPA® pump (Smiths Medical, Minn., U.S.A.). A gel may be contained in a cassette, pouch or vial that is attached to the pump to create a delivery system. The delivery system is connected to a duodenal tube or a jejunum tube for intra-intestinal administration. An example of a syringe type delivery system is the portable pump sold under the trade name Cane Crono Infusion Pump (Applied Medical Technology Ltd., Cambridge, U.K.).

In some embodiments, an intra-intestinal gel of the present invention may be administered continuously over a period of up to about 16 hours about 18 hours, about 20 hours, about 22 hours, about 24 hours per day. In some embodiments, an intra-intestinal gel of the present invention may be administered continuously for more than one day, a week, or a month.

In some embodiments, an intra-intestinal gel composition is administered so that it delivers a desired amount of one or more of its active agents in a day (e.g., in a 24 hour period).

Stability

One feature of certain embodiments of the present invention relates to the storage stability, or shelf life, of a pharmaceutical composition, and particularly of an intra-intestinal gel composition.

The shelf life of the prior art intra-intestinal gel LCIG (e.g., DUODOPA®) in refrigerated condition is basically determined by the degradation of carbidopa, and more specifically the level of the degradation product hydrazine which is considered to be genotoxic.

While levodopa has been found to be relatively stable in the prior art LCIG as well as in intra-intestinal gel compositions of the present invention, carbidopa has been found to degrade about 50 percent quicker in a corresponding intra-intestinal gel composition which additionally contains entacapone.

In some embodiments, levodopa/carbidopa/entacapone gel compositions of the invention provide surprising properties that hamper the formation of the final carbidopa degradation product (e.g., hydrazine). In some embodiments, compositions of the present invention may have an advantageously lowered hydrazine level (e.g., less than about 20 ppm, or less than about 30 ppm) after long term storage in refrigerated condition compared with the prior art intra-intestinal gel LCIG (e.g., DUODOPA®). In some embodiments, compositions of the present invention may have about 50% less hydrazine level compared with the prior art intra-intestinal gel LCIG (e.g., DUODOPA®).

In some embodiments, in such a gel composition entacapone will function not only as a COMT inhibitor but also as a hydrazine-formation inhibitor in degradation of carbidopa.

An increase of the stability of the levodopa/carbidopa/entacapone composition of the invention to have, for instance, a stability of about 10 weeks, about 15 weeks, about 20 weeks or about 25 weeks in a refrigerated condition, when active ingredients should still have a meaningful therapeutic effect, may be accomplished by different means, separately, or, optionally, by two or more of them in combination. In some embodiments, an increase of the stability of the levodopa/carbidopa/entacapone composition of the invention to have, for instance, a stability of about 18 hours, about 20 hours, about 22 hours, about 24 hours, about 26 hours, about 28 hours, or about 30 hours in room temperature (e.g., 25° C.).

According to some embodiments of invention, the stability of an intra-intestinal gel composition may be increased by adjusting the pH of the gel composition to not be higher than about 5.7 (i.e. equal to or lower than 5.7).

Generally, the stability of active substances (primarily carbidopa) in a gel composition increases as the pH is lowered. On the other hand, however, the stability of a gel per se decreases with lower pH (being destabilized by breaking down of the viscosity). Further, too low a pH value of a gel composition is detrimental to the patient's intestine.

According to some embodiments of invention, it has been found that increased storage stability with regard to active substances as well as to a gel structure and to the sensitivity of the patient's intestine is achieved by careful selection of the pH to be within an optimum range of from about 4.5 to about 5.7, preferably 4.5 to 5.5, for example about 5.0.

In some embodiments, acidic adjustment of the pH may be effected by a mineral acid, such as hydrochloric acid, or an organic acid, for example citric acid or citric buffer.

Alternatively, or in addition to pH stabilization, stabilization of a gel composition may be effected by oxygen removal which may be done by well known methods, typically by purging with nitrogen gas.

Yet an alternative way of stabilizing an intra-intestinal gel composition is to introduce one or more antioxidants, e.g., ascorbic acid or citric acid, into a gel. Other antioxidants that may be used may readily be selected by a person skilled in the art from commonly known antioxidants.

Storage of a gel composition in a light reducing container, such as an aluminum bag, has also been found to have some positive effect on the degradation of carbidopa and entacapone.

In some embodiments, an intra-intestinal gel composition of the invention has a pH of about 5, is deoxygenized with nitrogen gas, and is preferably provided in a light protected container.

Heavy metals are known to catalyse the degradation of carbidopa. While prior art levodopa/carbidopa formulations have been shown to be stabilized by EDTA, which has a great chelating property, the stability of the intra-intestinal gel composition of the invention has surprisingly been found to be negatively affected by EDTA. In some embodiments, gel compositions provided by the invention are therefore preferably free of any chelating agent.

Those of ordinary skill in the art, reading the present disclosure, will appreciate that its included demonstration of increased carbidopa stability in the presence of entacapone (and specifically in the presence of entacapone in a gel composition for intra-intestinal administration) may well be generalizable to presence of other COMT inhibitors, and/or to contexts other than combination in a gel format as described herein. Thus, in some embodiments, the present disclosure provides gel compositions (e.g., for intra-intestinal administration) comprising a pharmaceutically active agent that comprises or consists of carbidopa and a COMT inhibitor, and optionally further comprises levodopa. Furthermore, in some embodiments, the present disclosure provides therapeutic regimens in which administration of carbidopa is combined with administration of entacapone (e.g., in the context of a gel composition for intra-intestinal administration) or other COMT inhibitor, optionally in separate compositions, may reduce hydrazine levels (e.g., as compared with those observed under comparable conditions absent the COMT inhibitor, e.g., entacapone), with beneficial effects for patients.

Combination Therapy

As described herein, the present invention provides technologies that involve and/or achieve combination therapy with (a) a dopamine replacement agent; (b) one or more DDIs and (c) one or more COMT inhibitors. As described herein, in many embodiments, the present disclosure relates to administration of individual agents or combination agents for which certain therapeutic regimens and formats are already known. In some embodiments, insights embodied in the present disclosure provide compositions and/or dosing regimens that contain or include reduced dosing (e.g., in daily amount, total amount over a selected period, and/or frequency of dosing) relative to such known regimens and/or formats.

In certain embodiments, as described herein, each of (a) a dopamine replacement agent (b) a DDI; and (c) a COMT inhibitor are administered simultaneously, and even in a single composition (e.g., in an intra-intestinal gel composition as described herein). Teachings included herein provide those of ordinary skill in the art with insights and technologies (e.g., compositions and methods) that are not limited to the specific exemplified embodiments.

For example, teachings provided herein demonstrate to those of skill in the art, for example, that the (a) a dopamine replacement agent (b) a DDI; and (c) a COMT inhibitor might, in certain embodiments, be administered in separate compositions. In some embodiments, each may be in a distinct composition. In some embodiments, two may be together in a single composition while the third is in a separate composition. To give but one specific example, those skilled in the art, reading the present disclosure, would appreciate that co-administration of DUODOPA® with a separate intra-intestinal gel composition comprising entacapone, and/or another COMT inhibitor, might be desirable.

Of course, those skilled in the art will immediately be aware that not all advantages documented herein may be achieved, or achieved to the same level, in all such formats. That is, particular advantages may be attributable, at least in part, to co-localization of all three agents in a single composition. However, those skilled in the art will also recognize that significant benefit may also be achieved even without such co-localization. For example, co-administration (whether substantially simultaneous or separated in time but nonetheless achieving exposure of the patient, and optionally the same site within the patient [e.g., the duodenum] to all three agents), for example, of separate gels, may well provide significant benefit relative to other available therapeutic strategies.

Those of ordinary skill in the art, reading the present disclosure will particularly appreciate that, in some embodiments, depending on one or more features of the particular utilized (a) dopamine replacement agents (b) DDI; and (c) a COMT inhibitors, distinct dosing patterns might be beneficial in some contexts. For instance, different agents within a particular class may have different half-lives and/or other pharmacologic properties, such that their timing of administration relative to other agents might desirably be staggered. To give but one example, studies have reported different pharmacokinetic and pharmacodynamic properties for different COMT inhibitors (see, for example, Forsberg et al., JPET 304:498, 2003-02-01) and have reported, for instance that tolcapone has a longer duration of action and a better brain penetration than entacapone. Specifically, Forsberg et al report that:

"After intravenous administration (3 mg/kg), the elimination half-life ($t_{1/2\beta}$) of entacapone (0.8 h) was clearly shorter than that of tolcapone (2.9 h). The striatum/serum ratio of tolcapone was 3-fold higher than that of entacapone. After a single oral dose (10 mg/kg), both entacapone and tolcapone produced an equal maximal degree of COMT inhibition in peripheral tissues, but tolcapone inhibited striatal COMT more effectively than did entacapone. After the 7-day treatment (10 mg/kg twice daily), COMT activity had recovered to a level of 67 to 101% of control within 8 h after the last dose of entacapone. In tolcapone-treated animals, there was still extensive COMT inhibition present in peripheral tissues, and the degree of inhibition was higher than that attained after a single dose. The pharmacokinetic-pharmacodynamic modeling revealed that a plateau of COMT inhibition near the maximal attainable inhibition was reached already by plasma concentrations below 2000 ng/ml, both with entacapone and tolcapone. Entacapone and tolcapone inhibited equally rat liver COMT in vitro with $K_i$ values of 10.7 and 10.0 nM, respectively,"

and conclude that their results" suggest that peripheral COMT inhibitor is inhibited continuously when tolcapone is dosed at 12-h intervals, but this was not seen with entacapone."

One of ordinary skill in the art, aware of these differences and reading the present disclosure would appreciate that, for example, it might be desirable to dose tolcapone less frequently than entacapone. Given that the present disclosure demonstrates, among other things, particular utility of intra-intestinal gel administration of COMT inhibitors, and also demonstrates certain advantages of compositions that contain each of (a) a dopamine replacement agent (b) a DDI; and (c) a COMT inhibitor, those of ordinary skill in the art would appreciate that the disclosure provides combination compositions that include tolcapone (e.g., compositions that include each of levodopa, carbidopa, and tolcapone), optionally in a gel format, for example for intra-intestinal administration, and would also appreciate that, in some embodiments, it might be desirable to include a lower ratio of COMT inhibitor to other active agents when the COMT inhibitor is tolcapone as compared with entacapone. Alternatively, comparable ratios might be preserved, but less frequent dosing utilized, optionally for example interspersed with additional dosing of a composition that contained on the (a) dopamine replacement agents and (b) DDI.

Alternatively or additionally, one skilled in the art, reading the present disclosure, will appreciate the extent to which its teachings may be applied to and/or combined with administration of one or more of the (a) dopamine replacement agents (b) DDI; and (c) COMT inhibitor in the context of an already-available format (e.g., as described herein). Thus, for example, in some embodiments, therapeutic regimens provided by the present disclosure may utilize, for example, intra-intestinal administration of a gel composition comprising a COMT inhibitor (e.g., entacapone) in combination with (a) dopamine replacement agents (e.g., levodopa) and/or (b) a DDI (e.g., carbidopa) in the context of an available commercial format. In some such embodiments, route, timing, and/or amount of any individual dose (and/or of total doses) of the commercial format may be different when combined with the, intra-intestinal administration of a gel composition comprising a COMT inhibitor as provided herein.

Still further, one of ordinary skill in the art will readily appreciate that, in some embodiments, combination therapy as described herein, in accordance with which a patient receives therapy with each of (a) a dopamine replacement agent; (b) one or more DDIs and (c) one or more COMT inhibitors may be further combined with one or more other therapies/therapeutic modalities. Just to name a few, in some embodiments, provided therapy is administered in combination with one or more anticholinergics (e.g., antihistamines, topine, and/or esters thereof etc. and combinations thereof), one or more glutamate antagomists, and/or one or more amantadine derivatives. In some embodiments, one or more such agents are included in an intra-intestinal gel as described herein.

Bioavailability

In some embodiments, the present invention encompasses the insight that administering a combination of levodopa, a DDI, and a COMT inhibitor to a subject, wherein one or more of the agents in the combination is administered by intra-intestinal administration of a pharmaceutical gel, provides unexpected improvement of one or more pharmacokinetic properties (e.g., area under curve (AUC), bioavailability (e.g., absolute bioavailability, relative bioavailability), half-life, etc.) of one or more active agents.

Among other things, the present disclosure demonstrates the surprising discovery that provided compositions and/or methodologies can achieve significant improvement in bioavailability of a dopamine replacement agent (e.g., levodopa). Specifically, prior reports of combination therapy with the three-component combination of (a) levodopa, (b) carbidopa, and (c) entacapone in a single tablet can increase bioavailability of levodopa about 10% to about 30% as compared with an otherwise comparable tablet containing (a) levodopa and (b) carbidopa but lacking (c) entacapone. (see, for example, Summary of Product Characteristics of STALEVO®, http://www.ema.europa.edu/docs/en_GB/document_library/EPAR_-_Product_Information/human/00511/WC500057485.pdf, last visited Sep. 3, 2015) Table 1, below, summarizes certain literature reports observed increases in levodopa bioavailability upon combination with COMT inhibitors:

TABLE 1

Levodopa bioavailability increase
in the presence of COMT inhibitors

| Reference | COMT inhibitor | Levodopa bioavailablity increase |
| --- | --- | --- |
| Fine et al. 2000[16] | Tolcapone | 33% |
| Hobson et al. 2002[23] | Tolcapone | 25% |
| Vingerhoets et al. 2002[53] | Entacapone | 20% |
| Wenzelburger et al. 2002[56] | COMT inliibitor* | 30% |
| Brodsky et al. 2003[4] | COMT inhibitor* | 20% |
| Esselink et al. 2004[12] | Entacapone | 20% |
| Evans et al. 2004[13] | Entacapone | 33% |
| Reimer et al. 2004[47] | COMT inhibitor* | 30% |
| Möller et al. 2005[37] | Entacapone | 30% |
| Deuschi et al. 2006[10] | Entacapone | 33% |
| Ondo et al. 2006[42] | COMT inhibitor* | 10% |
| Katzenschlager et al. 2008[26] | Entacapone | 33% |
| Cabrini et al. 2009[5] | Entacapone | 33% |
| Peralta et al. 2009[46] | Entacapone | 20% |
| Fan et al. 2009[14] | COMT inliibitor* | 25% |

*The type of COMP inhibitor has not provided.

As can be seen with reference to the Examples section below, and particularly with reference to Example 4, the present disclosure documents the surprising finding that certain inventive gel compositions (e.g., formulated for intra-intestinal administration) including a pharmaceutically active agent that comprises or consists of each of (a) a dopamine replacement agent; (b) a DDI; and (a) COMT inhibitor can achieve a dramatically larger increase in levodopa bioavailability, indeed more than 40%, 45%, 50%, or even 55%, as an average increase of 55% (an improvement within the range of 1.5-3.0 fold) was observed, even in the single study described therein.

In light of these remarkable findings, one of ordinary skill in the art will appreciate that the present disclosure establishes that compositions and/or combinations can be identified, developed, provided, and/or characterized that also achieve improvement in one or more pharmacokinetic or pharmacodynamic properties of levodopa (and/or potentially one or more other dopamine replacement agents). The present disclosure provides technologies for achieve such identification, development, provision and/or characterization.

For example, in certain embodiments, those of ordinary skill in the art may follow guidance presented in Example 4 (viewed in context of the rest of the present specification) to test any of a variety of different DDI and/or COMT inhibitor agents, and combinations (e.g., different ratios, etc.) thereof, and assess their effect(s) on bioavailability and/or other parameters (e.g., stability, half-life, AUC over a selected period of time, etc.) of one or more dopamine replacement agents when administered to a model organism or human (and/or as evaluated in one or more appropriate models thereof).

Thus, the present disclosure provides, among other things, compositions comprising a dopamine replacement agent, a DDI and a COMT inhibitor, which is characterized by an improvement in one or more pharmacokinetic and/or pharmacodynamic features of the dopamine replacement agent when assessed in an appropriate system as compared with an appropriate reference composition. In some embodiments, an appropriate reference composition is an otherwise comparable composition lacking the COMT inhibitor, or including a different COMT, or including the same COMT inhibitor in a different amount (whether absolute or relative to the dopamine replacement agent, the DDI, or both). In some embodiments, an appropriate reference composition is an otherwise comparable composition lacking the DDI, or including a different DDI, or including the same DDI in a different amount (whether absolute or relative to the dopamine replacement agent, the COMT inhibitor, or both).

In some embodiments, an appropriate improvement has a magnitude of at least 10%, 20%, 30%, 40%, 50%, 60%, 70%, 75%, 80%, 85%, 90%, 95%, 100%, or more. In some embodiments, an appropriate improvement has a magnitude of at least 1.5×, 2.0×, 2.5×, 3.0×, 3.5×, 4.0×, 4.5×, 5.0×, 5.5×, 6.0×6.5×, 7.0×, 7.5×, 8.0×, 8.5×, 9.0×, 9.5×, 10×, or more.

In the following, non-limiting embodiments of an intra-intestinal gel composition of the present invention and comparative experiments therewith will be described.

EXAMPLES

Example 1: Compositions

In the following, experiments will be described performed with an embodiment of intra-intestinal gel composition according to the present invention, below referred to as "LECIGON™", and with the prior art commercial levodopa/carbidopa intra-intestinal gel, DUODOPA®, below referred to as "LCIG", as well as with modified LECIGON™ compositions for stability tests. The compositions of LCIG and LECIGON™ are given in Tables 2 and 3 below.

TABLE 2

| Exemplary composition of LCIG | |
| --- | --- |
| Substance | Amount |
| Micronized levodopa | 2% (w/w) (20 mg/ml) |
| Micronized carbidopa | 0.5% (w/w) (5.0 mg/ml) |
| NaCMC | 2.92% (w/w) |
| Purified water | 94.58% (w/w) |

TABLE 3

| Exemplary Compositions of LECIGON ™ | |
| --- | --- |
| Substance | Amount |
| Micronized levodopa | 2% (w/w) (20 mg/ml) |
| Micronized carbidopa | 0.5% (w/w) (5.0 mg/ml) |
| Micronized entacapone | 2% (w/w) (20 mg/ml) |
| NaCMC | 2.92% (w/w) |
| Purified water | 92.58% (w/w) |

15 exemplary small scale batches as described in Table 4 were manufactured as described below and filled into syringes for initial and stability evaluation in various storage and use conditions. The batch size of the experiments was 100 to 500 g. In Table 4, API is active pharmaceutical ingredient, L is levodopa, C is carbidopa, and E is entacapone.

TABLE 4

| Exp. | API (mg/g) | pH | Formulation |
| --- | --- | --- | --- |
| 1 | L: 20, C: 5 | 6.1 | Reference |
| 2 | L: 20, C: 5, E: 20 | 5.7 | Reference + Entacapone |
| 3 | L: 20, C: 5, E: 20 | 5.6 | 0.05% EDTA |
| 4 | L: 20, C: 5, E: 20 | 5.60 | 0.5% citric acid (NaOH for pH adjustment) |
| 5 | L: 20, C: 5, E: 20 | 5.75 | 0.1% ascorbic acid (NaOH for pH adjustment) |
| 6 | L: 20, C: 5, E: 20 | 5.03 | Low pH (target pH 5.0) |
| 7 | L: 20, C: 5, E: 20 | 7.0 | High pH (target pH 7.0) |
| 8 | L: 20, C: 5, E: 20 | 5.7 | Aluminium bag (composition 2) |
| 9 | L: 20, C: 5 | — | Reference with 0.5% citric acid + 0.05% EDTA |
| 10 | L: 20, C: 5, E: 20 | 5.6 | 0.5% citric acid + 0.05% EDTA |
| 11 | L: 20, C: 5, E: 20 | 5.86 | Reference LECIGON ™ |

TABLE 4-continued

| Exp. | API (mg/g) | pH | Formulation |
| --- | --- | --- | --- |
| 12 | L: 20, C: 5, E: 20 | 5.5 | 0.5% citrate buffer (citric acid/sodium citrate) |
| 13 | L: 20, C: 5, E: 20 | 5.0 | 0.5% citrate buffer (low pH) |
| 14 | L: 20, C: 5, E: 20 | 5.75 | 0.1% ascorbic Acid + 0.05% EDTA |
| 15 | L: 20, C: 5, E: 20 | 5.86 | Deoxydation using $N_2$ |

Example 2: Manufacturing Process

The exemplary manufacturing process of intra-intestinal gel samples to be tested is described below.

1) Sodium carboxymethyl cellulose was added to purified water in a Pyrex beaker during homogenization for 1-2 minutes until a lump free viscous solution was achieved.
2) The active ingredients levodopa, carbidopa and entacapone were added and homogenized until a homogenous suspension was achieved.
3) Additional excipients as described in Table 3 above were added during homogenization until dissolved.
4) If needed, the pH was adjusted to the target by addition of sodium hydroxide or hydrochloric acid solution during mixing.
5) Manual filling of the suspension into syringes.

The process equipment used for manufacturing of the experimental batches included a Silverson L5M Homogenizer (Silverson Machines Ltd., Chesham, U.K.), and a IKA Janke & Kunkel RW28W Mixer (IKA Works GmbH, Staufen, Germany).

The following analytical equipment was used for physical analysis and in process controls during the manufacturing:
pH-meter—Mettler Toledo Seven Compact™ with Inlab Micro electrode (Mettler-Toledo Inc., Columbia, Ohio, U.S.A.).
Viscometer—Brookfield DV-I™ Prime with small sample adapter (Brookfield Engineering, Middleborough, Mass., U.S.A.).
HPLC—Agilent 1100 with DAD detector and cooled injector; OpenLAB CDS Chemstation C.01.05 (Agilent Technologies Inc., Santa Clara, Calif., U.S.A.).

Example 3: Stability Tests

This example demonstrates stability of intra-intestinal gels under various conditions.
3.1. Stability of Unstabilized LECIGON™ Vs LCIG
The stability of unstabilized LECIGON™ was compared with that of LCIG with regard to the stability of carbidopa, especially its degradation product hydrazine which is considered to be genotoxic. Hydrazine is formed in equal molar number as 3,4-dihydroxyphenylacetone (DHPA), which is easier to measure and was therefore used as reference in this as well as in the other experiments below. The results are shown in Table 5 below.

TABLE 5

| | | DHPA (area % of carbidopa) | |
| --- | --- | --- | --- |
| Exp. | Formulation | 5 days at 25° C. | 10 days at 25° C. |
| 1 | LCIG: 20/5 mg/ml levodopa/carbidopa suspension | 3.08 | 5.1 |

TABLE 5-continued

|     |                                                                 | DHPA (area % of carbidopa) | |
| --- | --------------------------------------------------------------- | ------------------- | ------------------- |
| Exp. | Formulation                                                    | 5 days at 25° C.    | 10 days at 25° C.   |
| 2   | LECIGON ™: 20/5/20 mg/ml levodopa/carbidopa/entacapone suspension | 4.76              | 7.65                |
|     | Comparing 1 with 2                                              | +55%                | +50%                |

As shown in Table 5, carbidopa degrades about 50% quicker in the triple levodopa-carbidopa-entacapone gel suspension (LECIGON™) compared to a corresponding levodopa-carbidopa gel suspension (LCIG).

3.2. Stabilization of LECIGON™

Stabilization experiments with LECIGON™ with regard to carbidopa, levodopa and entacapone were performed in an accelerated stability study at 25° C. for 12 days. As reference product, LECIGON™ having no stabilizing modification was used. In addition to determination of DHPA, an additional carbidopa degradation product, 3,4-dihydroxyphenyl-propionic acid (DHPPA), as well as an (so far) unidentified degradation product of entacapone were measured.

The following stabilizing modifications of the LECIGON™ composition were tested, the corresponding experimental compositions ("Exp.") in Table 4 above being given within parentheses:

1. Varied pH (Exp. 6, 7)
2. Addition of anti-oxidant
    a) 0.1% ascorbic acid (Exp. 5)
    b) 0.5% citrate buffer (Exp. 12)
    c) 0.5% citric acid (Exp. 4)
3. Removal of oxygen
    nitrogen gas (Exp. 15)
4. Removal of metal ions
    0.05% EDTA (Exp. 3)
5. Combination of reduced pH and anti-oxidant (Exp. 13)
6. Combination of anti-oxidant and removal of oxygen
    a) 0.1% ascorbic acid and 0.05% EDTA (Exp. 14)
    b) 0.5% citric acid and 0.05% EDTA (Exp. 10)
7. Enclosure in an aluminium bag (Exp. 8).

The results are presented in Table 6 below. The results are ranked with respect to reduction of hydrazine (DHPA, RRT 7.1). RRT 8.5 is DHPPA, and RRT 11.8 is a degradation product of entacapone. Levodopa was stable in all combinations and is therefore not included in the table. In the table, "Carb" is carbidopa, and "Ent" is entacapone.

TABLE 6

|     | Formulation LECIGON ™ = 20/5/20 mg/ml of levodopa/ | Degradation products from | | | |
| --- | --- | --- | --- | --- | --- |
|     |     | Carbidopa | | Ent. | |
|     |     | DHPA RRT 7.1 | RRT 8.5 | RRT 11.8 | |
| Exp. | carbidopa/entacapone | | | | Comment |
| 6   | LECIGON ™ + Low pH (pH 5.0) | −73% | −77% | −76% | Reduction in pH has the clearest positive impact on both Carb and Ent |
| 5   | LECIGON ™ + 0.1% ascorbic acid (NaOH for pH-adjustment) | −42% | −10% | −25% | Ascorbic acid has a clear positive impact on the stability of both Carb and Ent |
| 15  | LECIGON ™ deoxygenized with $N_2$ | −37% | −12% | −42% | Deoxygenized suspension with $N_2$ has a clear positive impact on both Carb and Ent |
| 12  | LECIGON ™ + 0.5% citrate buffer (citric acid/sodium citrate) | 1% | −13% | −23% | Citrate buffer has a positive impact on both, more so om Ent |
| 4   | LECIGON ™ + 0.5% citric acid (NaOH for pH-adjustment) | 2% | −17% | −9% | Citrate acid has a slight positive impact on both Carb and Ent |
| 3   | LECIGON ™ + 0.05% EDTA | 20% | 32% | 38% | EDTA has a negative impact on the stability of both Carb and Ent |
| 7   | LECIGON ™ + High pH (pH 7.0) | 109% | 713% | 703% | Increased pH has the clearest negative impact on both Carb and Ent |
| 13  | LECIGON ™ + 0.5% citrate buffer (pH 5) | −9% | −78% | −74% | Citrate buffer in a combination with a low pH has a positive effect on both Carb and Ent. However the combination does not offer any benefits compared to only reducing pH. |
| 14  | LECIGON ™ + 0.1% ascorbic Acid + 0.05% EDTA | 10% | −49% | −45% | Ascorbic acid in combination with EDTA has a positive effect on Ent and one degradation product form Carb, however negative on DHPA. |
| 8   | LECIGON ™ + Aluminium bag (formulation 2) | −2% | −8% |  | Aluminium bag has minor impact on both Carb and Ent, likely due to reduced light exposure. |
| 10  | LECIGON ™ + 0.5% citric acid + 0.05% EDTA | 29% | 85% |  | A combination of both citric acid and EDTA has a negative impact on both carbidopa and entacapone |

3.3. pH Impacting Effect on the Stability of LECIGON™ pH was measured using a pH (glass) electrode. Indicated pH refers measurement for the final product.

Figure 2:
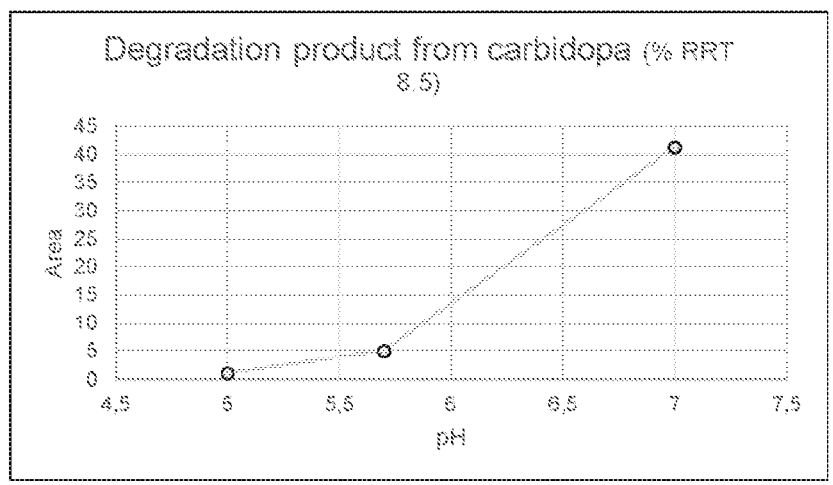
FIG. 2 is a graph showing an exemplary level of carbidopa degradation product DHPPA versus pH at the end of a 10 days stability test at 25° C. on a levodopa/carbidopa/entacapone gel formulation.
Figure 3:
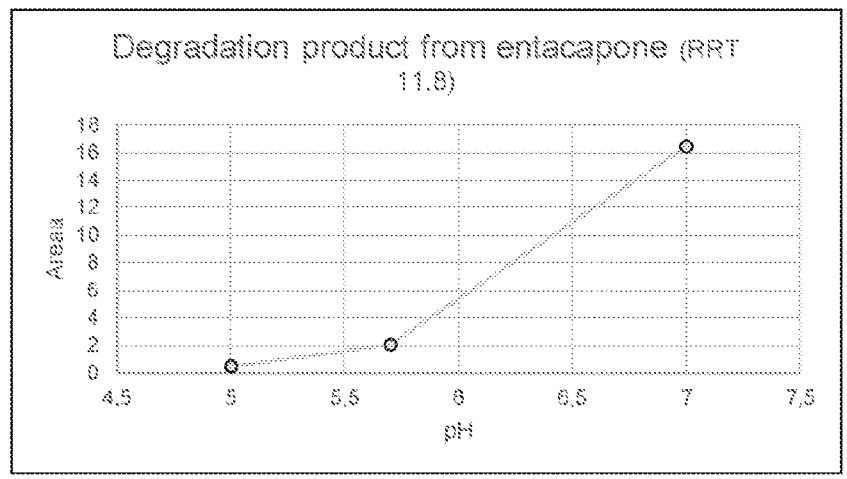
FIG. 3 is a graph showing an exemplary level of entacapone degradation product RRT 11.8 versus pH at the end of a 10 days stability test on a levodopa/carbidopa/entacapone gel formulation.

As shown in Table 6 above, pH has the greatest impact on the stability of both carbidopa and entacapone, its impact, however, being reduced with a reduced pH. The level of degradation products formed at the end of an accelerated stability study, 10 days at 25° C., at different pH of the gel suspension are shown in FIG. 1 (Carbidopa: DHPA), FIG. 2 (Carbidopa: RRT 8.5=DHPPA), and FIG. 3 (RRT 11.8).

3.4. Viscosity

Figure 4:
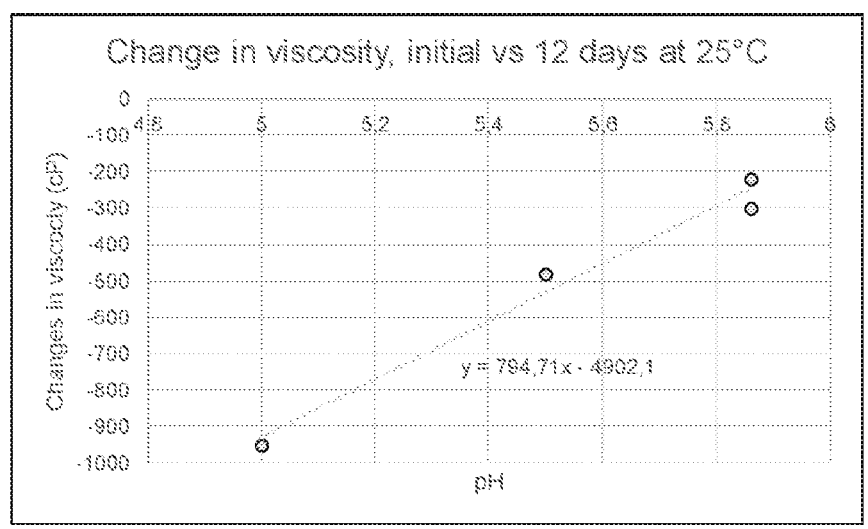
FIG. 4 is a graph showing an exemplary level of reduced viscosity versus pH at the end of a 12 days stability test on a levodopa/carbidopa/entacapone gel formulation.

While, as demonstrated above, a lower pH has a positive impact on the stability of both carbidopa and entacapone, however, a lower pH breaks down the viscosity of the NaCMC gel. FIG. 4 shows the level of reduced viscosity at end of an accelerated stability study, 12 days at 25° C., at different pH of the gel suspension.

3.5. Stability of LECIGON™, Summary

According to the test results obtained, the final formulation should have a reduced pH. A reduced pH, however, has two main drawbacks. Firstly, it breaks down the viscosity which destabilizes the suspension (sedimentation), the lower the pH is the quicker the gel breaks down, and secondly, a low pH may cause an irritation of the intestine at the site of administration. A viscosity reduction of maximum 1000 cP after 12 days would be acceptable which corresponds to a pH of about 4.9-5.0.

A pH of about 5 will likely not cause any irritation at the site of administration considering, among other things, the low daily volume of LECIGON™ administered (100 ml) compared to the about 10 liter of gastric juice passing the intestine per day, the gastric juice in addition being buffered.

Therefore, a suspension having a pH of about 5, stabilized with citric acid, deoxygenized with $N_2$, and having a container with light protection will likely give the best possible stability. A suitable alternative is a suspension having a pH of about 5, stabilized with ascorbic acid, deoxygenized with $N_2$, and having a container with light protection.

Heavy metals are known to catalyse the degradation of carbidopa. It is well known that EDTA has a great chelating property and that EDTA has shown stabilizing effects on carbidopa in a levodopa—carbidopa formulation. It was therefore surprising that EDTA had a negative impact on the stability of the present intra-intestinal gel formulation.

3.6 Long Term Storage Stability in Refrigerated Condition

A. Stability of LECIGON™ vs LCIG

Figure 5:
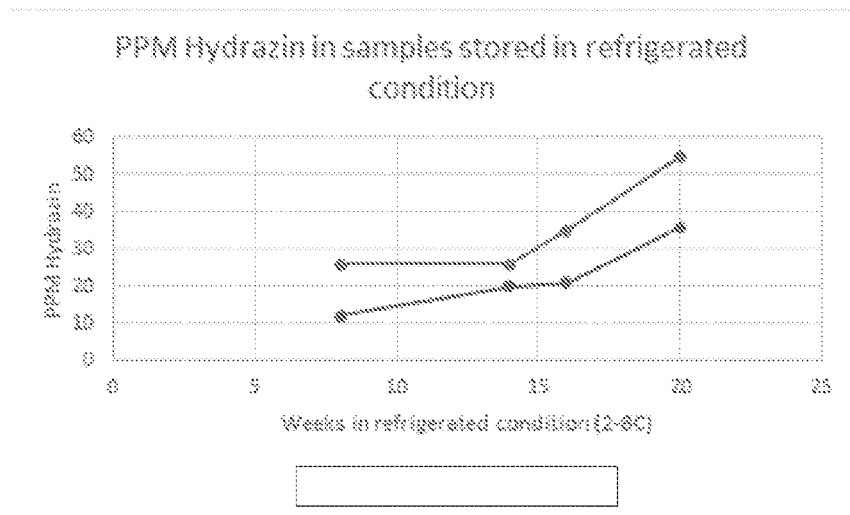
FIG. 5 is a graph showing exemplary levels of carbidopa degradation product hydrazine during a 20 weeks storage stability test in refrigerated condition (2-8° C.) on a levodopa/carbidopa gel formulation (upper curve) and a levodopa/carbidopa/entacapone gel formulation (lower curve).

The stabilities of samples of pH-stabilized LECIGON™ (pH 5.5) and LCIG were subjected to a 20 weeks storage test in refrigerated condition at 2-8° C. with regard to hydrazine formation. The hydrazine levels of the samples were measured at 14, 16 and 20 weeks. The results are shown in FIG. 5, where the upper curve indicates the hydrazine levels for LCIG and the lower curve the hydrazine levels for LECIGON™.

Since as demonstrated in Table 4 above, carbidopa degrades quicker in LECIGON™ than in LCIG, the level of hydrazine would theoretically be higher than in LCIG. The lower hydrazine levels obtained for LECIGON™ therefore indicate that the formation of hydrazine is inhibited by the presence of entacapone in the gel formulation.

B. Stability of LECIGON™ at Different pH Values

Figure 6:
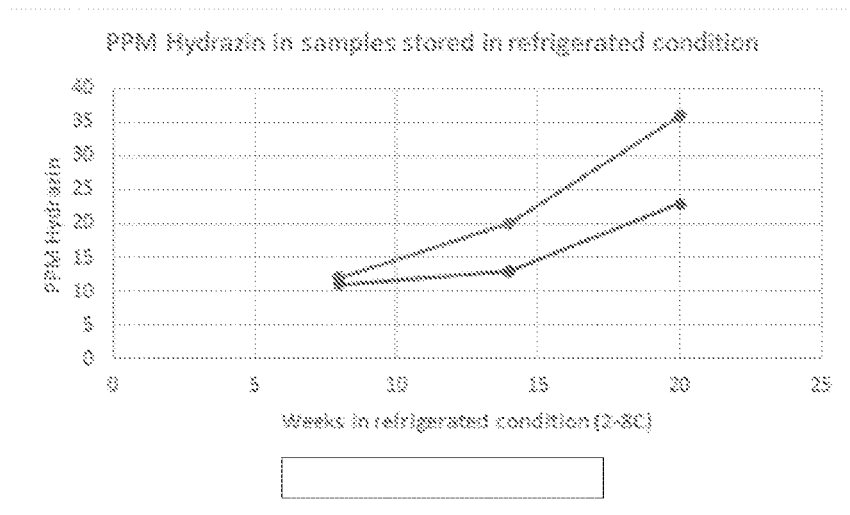
FIG. 6 is a graph showing exemplary levels of carbidopa degradation product hydrazine during a 20 weeks storage stability test in refrigerated condition (2-8° C.) on two levodopa/carbidopa/entacapone gel formulations of different pH; upper curve pH 5.5 and lower curve pH 5.0.

The stability of LECIGON™ samples stabilized at pH 5.5 or 5.0, respectively, with regard to hydrazine formation was studied in a similar 20 weeks storage test in refrigerated condition as in A above. The hydrazine levels of the samples were measured at 8, 14 and 20 weeks. The results are shown in FIG. 6, the upper curve showing the pH levels at pH 5.5, and the lower curve hydrazine levels at 5.0. As could be expected from the stability experiments on LECIGON™ presented further above, the hydrazine level at 20 weeks is considerably lower for the LECIGON™ formulation at pH 5.0.

Example 4: Pharmacokinetic Studies of LECIGON™

Two samples were used for pharmacokinetic studies: a gel with levodopa and carbidopa (DUODOPA® containing 20 mg/ml of levodopa, and 5 mg/ml of carbidopa), and the other gel with levodopa, carbidopa and entacapone (LECIGON™ containing 20 mg/ml of levodopa, 5 mg/ml of carbidopa, and 20 mg/ml of entacapone). All 11 patients received both treatments randomized, two days in a row. All patients were already on the DUODOPA® treatment and optimized on DUODOPA® treatment (individual doses). LECIGON™ doses were reduced to 80% of the optimized DUODOPA® dose to avoid patient becoming too hyperkinetic. Plasma concentration was measured at hour (from start of treatment) 0, 0.5, 1, 1.5, 2, 2.5, 3, 4, 5, 6, 7, 8, 9, 10, 11, 12, 13, 14, 14.5, 15, 15.5, 16, 16.5, 17 and 24 hours.

Figure 7:
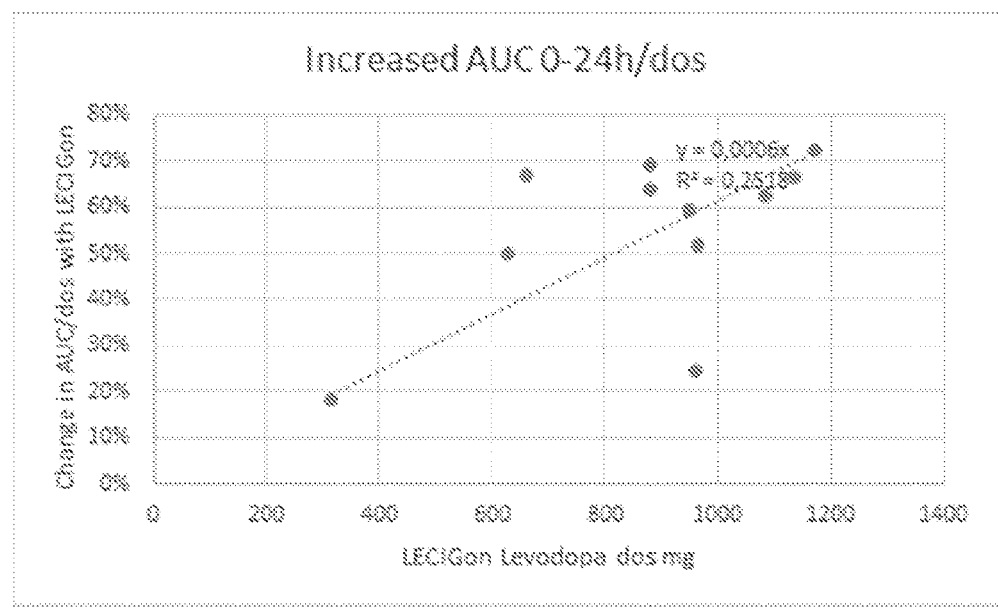
FIG. 7 is a graph showing exemplary pharmacokinetic studies of LECIGON™ vs DUODOPA®. Y-axis depicts LECIGON™'s Area Under Curve (AUC) increase per dose of levodopa compared to DUODOPA® (i.e., bioavailability increase). X-axis depicts levodopa dose of LECIGON™.

The bioavailability of levodopa is expected to increase with 10-30% (Summary of Product Characteristics of STALEVO®, http://www.ema.europa.eu/docs/en_GB/document_library/EPAR_-_Product_Information/human/000511/WC500057485.pdf, last visited Sep. 3, 2015) if it is given in combination with entacapone and carbidopa in a tablet form. As shown in Table 7 and FIG. 7, continuously administered LECIGON™ increased AUC of levodopa 55% on average, which is higher than the expected increase (e.g., 10-30%) as discussed above. LECIGON™ enables entacapone to increase levodopa's AUC efficiently. Without wishing to be bound by any particular theory, it is proposed that, as entacapone has a longer $t_{1/2}$ life than levodopa, entacapone inhibits catechol-O-methyltransferase until all levodopa is metabolized.

TABLE 7

| Subject ID | LECIGON ™ AUC 0-24 hours (h * ng/ml per mg of levodopa) | DUODOPA ® AUC 0-24 hours (h * ng/ml per mg of levodopa) | Increased AUC/dose with LECIGON ™ |
|---|---|---|---|
| 105 | 33.3 | 28.2 | 18% |
| 104 | 45.3 | 30.2 | 50% |
| 106 | 72.9 | 43.6 | 67% |
| 109 | 69.3 | 42.4 | 64% |
| 111 | 67.9 | 40.2 | 69% |
| 102 | 98.2 | 61.6 | 59% |
| 110 | 35.2 | 28.3 | 25% |
| 103 | 39.6 | 26.0 | 52% |
| 108 | 54.2 | 33.3 | 63% |
| 101 | 49.1 | 29.5 | 67% |
| 107 | 74.9 | 43.5 | 72% |
| Average | 58.2 | 37.0 | 55% |

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A pharmaceutical composition for intra-intestinal administration, comprising a dopamine replacement agent selected from levodopa, melevodopa, etilevodopa and combinations thereof, a dopamine decarboxylase inhibitor (DDI) wherein the dopamine decarboxylase inhibitor is carbidopa, benzerazide or combination thereof, and a catechol-O-methyltransferase (COMT) inhibitor selected from entacapone, tolcapone, opicapone and combinations thereof; and wherein the pharmaceutical composition comprises about 1.0 to about 15% (w/w) micronized dopamine replacement agent, about 0.1 to about 2.0% (w/w) micronized DDI, about 1.0 to about 5.0% (w/w) micronized COMT inhibitor, and about 1.0 to about 7.5% (w/w) sodium carboxymethyl cellulose.

2. The pharmaceutical composition of claim 1, wherein:
the pharmaceutical composition has a pH of about 5.7 or less;
the pharmaceutical composition is deoxygenized;
the pharmaceutical composition further comprises an antioxidant;
the pharmaceutical composition is free from metal chelating agent; and/or
the pharmaceutical composition is provided in a light-protected container.

3. The pharmaceutical composition of claim 1, wherein the composition has a pH of about 4.5 to about 5.5.

4. The pharmaceutical composition of claim 1, wherein the pharmaceutical composition further comprises an antioxidant, wherein said antioxidant is ascorbic acid or citric acid.

5. The pharmaceutical composition of claim 1, wherein the dopamine replacement agent, the DDI, and the COMT inhibitor are in the form of particles, wherein the particles are suspended in an aqueous carrier, and have a particle size no greater than 80 μm; and the aqueous carrier has a viscosity of at least 300 mPas at a moderate shear rate.

6. The pharmaceutical composition of claim 5, wherein the aqueous carrier comprises a polysaccharide selected from the group consisting of cellulose, methyl cellulose, ethyl cellulose, carboxymethyl cellulose, salts thereof, and combinations thereof.

7. The pharmaceutical composition of claim 6, wherein the aqueous carrier comprises sodium carboxymethyl cellulose.

8. The pharmaceutical composition of claim 5, wherein the pH of the pharmaceutical composition is greater than about 5.0, and the viscosity of the aqueous carrier after 12 days at 25° C. is at least about 300 mPas at a moderate shear rate.

9. The pharmaceutical composition of claim 1, wherein the weight ratio of DDI to COMT inhibitor is about 1:10 to about 1:2, or about 1:5 to about 1:3.

10. The pharmaceutical composition of claim 1, wherein the weight ratio of COMT inhibitor to dopamine replacement agent is about 10:1 to about 2:1, or 5:1 to 3:1.

11. A pharmaceutical composition for intra-intestinal administration, comprising about 20 mg/ml of dopamine replacement agent, about 5 mg/ml of DDI, and about 20 mg/ml of COMT inhibitor.

12. The pharmaceutical composition of claim 11, wherein the pharmaceutical composition has a pH of about 4.5 to about 5.5.

13. The pharmaceutical composition of claim 11, wherein the dopamine replacement agent, the DDI, and the COMT inhibitor are in the form of particles, wherein the particles are suspended in an aqueous carrier, and have a particle size no greater than 80 μm; and the aqueous carrier has a viscosity of at least 300 mPas at a moderate shear rate.

14. The pharmaceutical composition of claim 13, wherein the aqueous carrier comprises a polysaccharide selected from the group consisting of cellulose, methyl cellulose, ethyl cellulose, carboxymethyl cellulose, salts thereof, and combinations thereof.

15. The pharmaceutical composition of claim 14, wherein the aqueous carrier comprises sodium carboxymethyl cellulose.

16. The pharmaceutical composition of claim 11, wherein the pH of the pharmaceutical composition is greater than about 5.0, and the viscosity of the aqueous carrier after 12 days at 25° C. is at least about 300 mPas at a moderate shear rate.

17. A method of treating a neurodegenerative disease comprising administering intra-intestinally a pharmaceutical composition of claim 1 to a subject in need thereof.

18. A method of treating Parkinson's Disease, Alzheimer's Disease, or Huntingtop's Disease comprising administering intra-intestinally a pharmaceutical composition of claim 1 to a subject in need thereof.

19. The pharmaceutical composition according to claim 1 wherein the composition is in the form of a gel suspension.

20. A method of treating a neurodegenerative disease comprising administering intra-intestinally a pharmaceutical composition of claim 15 to a subject in need thereof.

21. A method of treating Parkinson's Disease, Alzheimer's Disease, or Huntington's Disease comprising administering intra-intestinally a pharmaceutical composition of claim 15 to a subject in need thereof.

22. The pharmaceutical composition according to claim 15 wherein the composition is in the form of a gel suspension.

* * * * *